(12) United States Patent
Nakaso et al.

(10) Patent No.: US 7,368,848 B2
(45) Date of Patent: May 6, 2008

(54) SURFACE ACOUSTIC WAVE DEVICE AND ENVIRONMENTAL DIFFERENCE DETECTING APPARATUS USING THE SURFACE ACOUSTIC WAVE DEVICE

(75) Inventors: Noritaka Nakaso, Tokyo (JP); Kazushi Yamanaka, 6-3, Katsura 2-chome, Izumi-ku, Sendai-shi, Miyagi 981-3134 (JP)

(73) Assignees: Toppan Printing Co., Ltd., Tokyo (JP); Kazushi Yamanaka, Sendai (JP)

( * ) Notice: Subject to any disclaimer, the term of this patent is extended or adjusted under 35 U.S.C. 154(b) by 0 days.

(21) Appl. No.: 11/812,373

(22) Filed: Jun. 18, 2007

(65) Prior Publication Data

US 2007/0247021 A1 Oct. 25, 2007

Related U.S. Application Data

(60) Division of application No. 11/377,615, filed on Mar. 17, 2006, now Pat. No. 7,247,969, which is a continuation of application No. PCT/JP2004/013755, filed on Sep. 21, 2004.

(30) Foreign Application Priority Data

Sep. 19, 2003 (JP) ............... 2003-327950
Sep. 19, 2003 (JP) ............... 2003-327951

(51) Int. Cl.
*H01L 41/187* (2006.01)
*H01L 41/04* (2006.01)

(52) U.S. Cl. .................. 310/313 R; 310/313 A

(58) Field of Classification Search ........... 310/313 R, 310/313 A, 313 B, 313 C, 313 D, 357–360
See application file for complete search history.

(56) References Cited

U.S. PATENT DOCUMENTS 5,698,927 A 12/1997 Tanaka et al.
6,566,787 B2 5/2003 Tsukahara et al.

(Continued)

FOREIGN PATENT DOCUMENTS

JP 57-41842 9/1982

(Continued)

OTHER PUBLICATIONS

International Preliminary Report on Patentability, dated Mar. 30, 2006.

(Continued)

*Primary Examiner*—Derek J. Rosenau

(57) ABSTRACT

A surface acoustic wave device includes a three-dimensional substrate having an annular curved surface enabling to propagate a surface acoustic wave, and an electro-acoustic transducing element, which excites and propagates the surface wave along the surface, and receives the propagated surface wave. The substrate is made of a $Li_2B_4O_7$, $Bi_{12}SiO_{20}$, $LiNbO_3$, $LiTaO_3$, or quartz crystal, and the element propagates the surface wave along a line of intersection between a crystal face of the crystal and the surface, and the line of intersection is defined as an outermost circumferential line of the surface. An environmental difference detecting apparatus uses the device having a plurality of propagating surface zones and compares surface acoustic wave reception signals of electro-acoustic transducing elements in the propagating surface zones of the device with each other, and detects an environmental difference in space portions with which the propagating surface zones come into contact.

14 Claims, 14 Drawing Sheets

U.S. PATENT DOCUMENTS

| | | | |
|---|---|---|---|
| 6,950,584 B1 * | 9/2005 | Suzuki | 385/122 |
| 2002/0014809 A1 | 2/2002 | Tsukahara et al. | |
| 2002/0079989 A1 | 6/2002 | Kadota et al. | |
| 2004/0189148 A1 * | 9/2004 | Yamanaka et al. | 310/313 R |

FOREIGN PATENT DOCUMENTS

| | | |
|---|---|---|
| JP | 62-13021 | 8/1994 |
| JP | 2003-115743 | 4/2003 |
| JP | 2003-115744 | 4/2003 |
| WO | WO 01/45255 | 6/2001 |

OTHER PUBLICATIONS

International Preliminary Report on Patentability, dated Jun. 26, 2006.
U.S. Appl. No. 11/377,615, filed Mar. 17, 2006, Noritaka Nakaso, et al., Toppan Printing Co. Ltd. Kazushi Yamanaka.
U.S. Appl. No. 11/812,374, filed Jun. 18, 2007, Noritaka Nakaso et al., Toppan Printing Co. Ltd. Kazushi Yamanaka.
U.S. Appl. No. 11/812,369, filed Jun. 18, 2007, Noritaka Nakaso et al., Toppan Printing Co. Ltd. Kazushi Yamanaka.
U.S. Appl. No. 11/812,370, filed Jun. 18, 2007, Noritaka Nakaso et al., Toppan Printing Co. Ltd. Kazushi Yamanaka.
U.S. Appl. No. 11/812,367, filed Jun. 18, 2007, Noritaka Nakaso et al., Toppan Printing Co. Ltd. Kazushi Yamanaka.

* cited by examiner

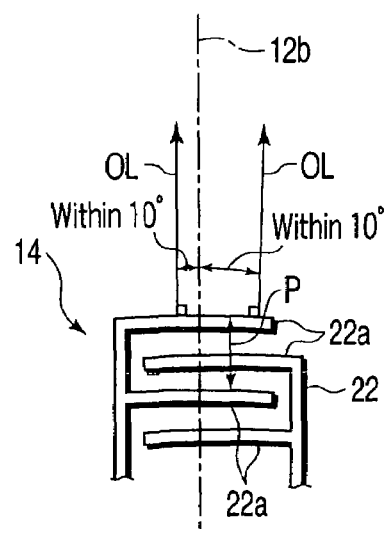
F I G. 5
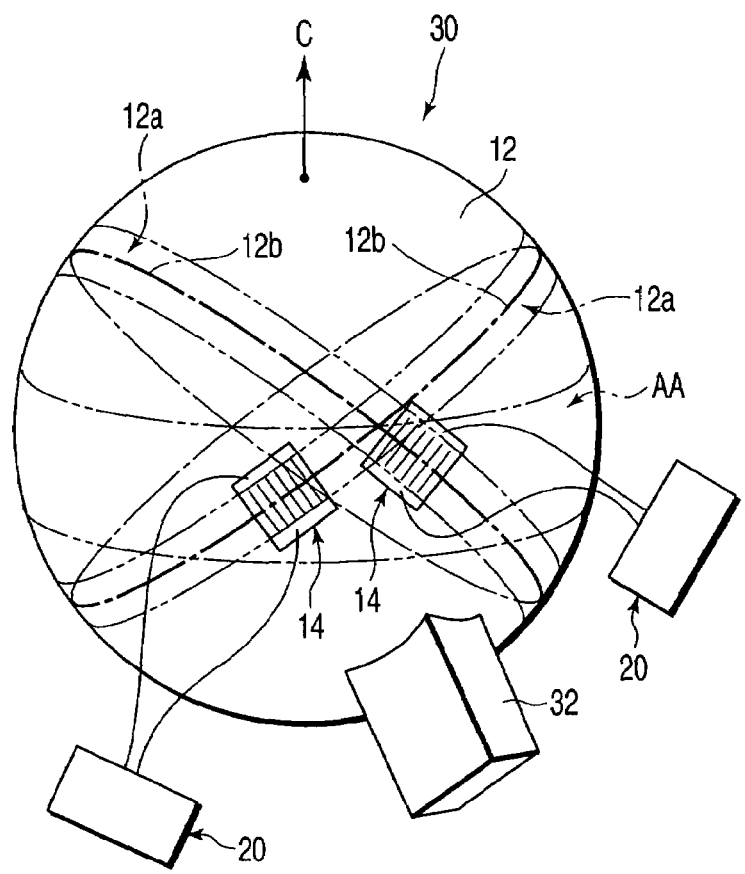
F I G. 6

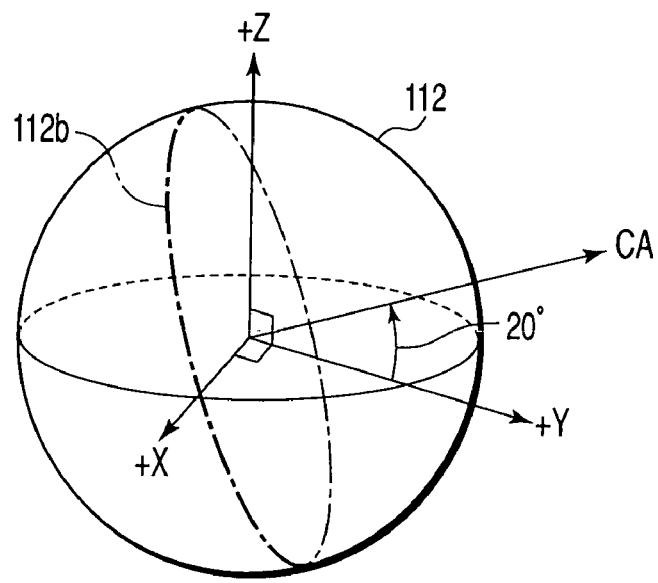
F I G. 12
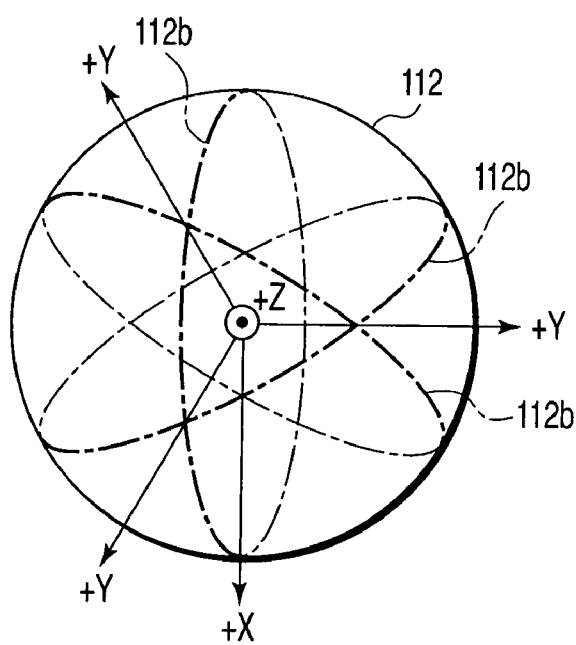
F I G. 13

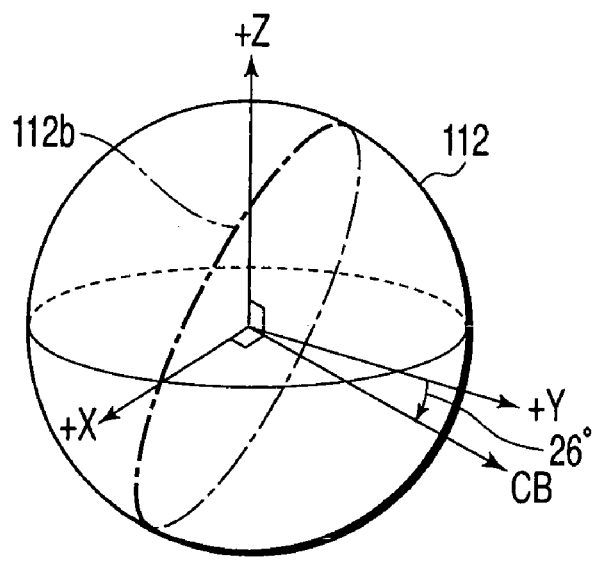
F I G. 14
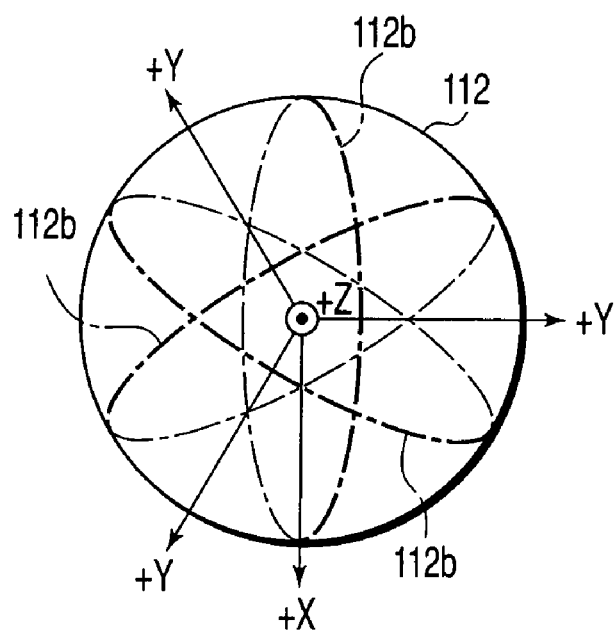
F I G. 15

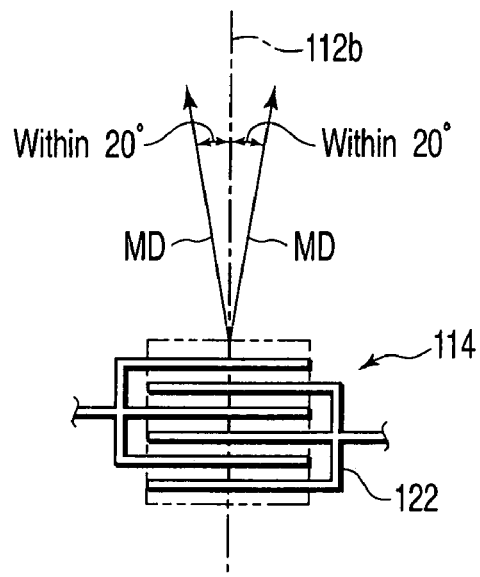
F I G. 16
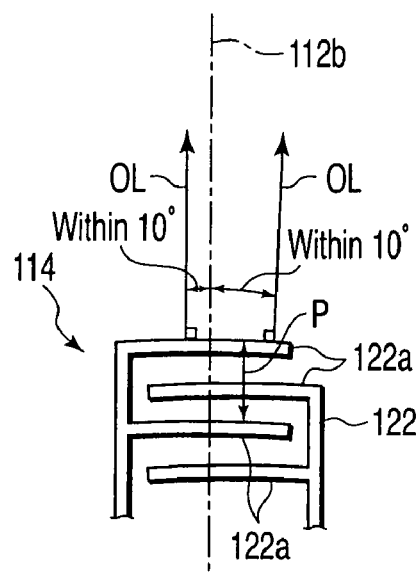
F I G. 17

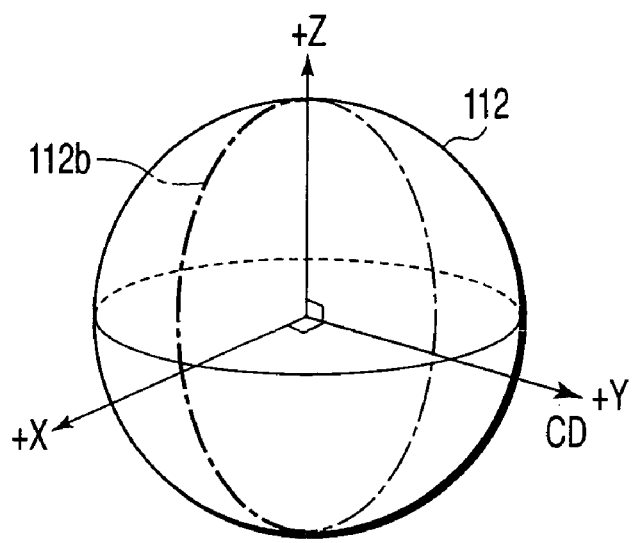
F I G. 20
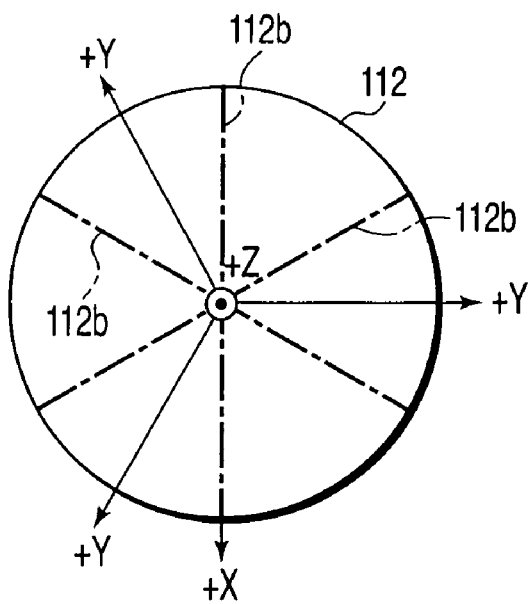
F I G. 21

SURFACE ACOUSTIC WAVE DEVICE AND ENVIRONMENTAL DIFFERENCE DETECTING APPARATUS USING THE SURFACE ACOUSTIC WAVE DEVICE

CROSS-REFERENCE TO RELATED APPLICATIONS

This application is a divisional of U.S. application Ser. No. 11/377,615 filed Mar. 17, 2006 now U.S. Pat. No. 7,247,969, which is a continuation application of PCT application no. PCT/JP2004/013755, filed Sep. 21, 2004, which is based upon and claims the benefit of priority from prior Japanese patent applications no. 2003-327950, filed Sep. 19, 2003; and no. 2003-327951, filed Sep. 19, 2003, the entire contents of the foregoing being incorporated herein by reference.

BACKGROUND OF THE INVENTION

1. Field of the Invention

The present invention relates to a surface acoustic wave device, and an environmental difference detecting apparatus using the surface acoustic wave device.

2. Description of the Related Art

Conventionally, there is well known a surface acoustic wave device comprising: a substrate having a surface capable of exciting a surface acoustic wave (SAW) and propagating the excited surface acoustic wave: and an electro-acoustic transducing element capable of exciting the surface acoustic wave along a surface of the substrate, propagating the surface acoustic wave along the surface, and receiving the propagated surface acoustic wave.

A surface acoustic device is used as a delay line, an oscillating device, a resonating device, a frequency selecting device, a variety of sensors including, for example, a chemical sensor, a biological sensor and a pressure sensor, or a remote tag, etc.

International Publication WO 01/45255 discloses a spherically shaped surface acoustic wave device. A substrate of the spherically shaped surface acoustic device has a spherically shaped surface capable of exciting a surface acoustic wave and propagating the excited surface acoustic wave. An electro-acoustic transducing element of the spherically shaped surface acoustic wave device is arranged in a band shaped zone having a predetermined width and being continuous in an annular shape on the spherically shaped surface of the substrate. The electro-acoustic transducing element is configured to propagate the surface acoustic wave excited along the surface in a direction in which the band shaped zone is continuous, and to repeatedly circulate the propagated wave.

The spherically shaped surface acoustic wave device can repeatedly circulate the surface acoustic wave, which is excited by the electro-acoustic transducing element in the band shaped surface acoustic wave propagating zone of the substrate that is continuous in the annular shape, in the band shaped zone without substantially attenuating the surface acoustic wave.

In order to propagate a surface acoustic wave along a surface of a substrate of a surface acoustic wave device, the whole substrate is made of a material capable of being excited to generate a surface acoustic wave and capable of propagating the excited surface acoustic wave, or alternatively is made by adhering a thin film, which is formed of a material capable of being excited and propagating a surface acoustic wave, on its surface.

It is known that the substrate formed of a combination with the thin film is high in manufacturing cost and is unsuitable for a mass-production at the present stage. It is also known that, in the substrate formed of only the material capable of being excited and propagating the surface acoustic wave, a difference occurs in a performance of propagating the surface acoustic wave such that the surface acoustic wave cannot be propagated or circulated depending on a direction in which an attempt is made to propagate the surface acoustic wave. Along the surface, it is difficult to propagate or circulate the surface acoustic wave in a plurality of different directions from each other.

The present invention has been made under the above-described circumstances, and an object of the present invention is to provide a surface acoustic wave device suitable to a mass-production and capable of always stably achieving a good surface acoustic wave propagation performance, and an environmental difference detecting apparatus using the surface acoustic wave device.

BRIEF SUMMARY OF THE INVENTION

In order to achieve the above described object, a surface acoustic wave device according to this invention comprises:

a three-dimensional substrate having a surface, which includes at least a part of an annular curved surface formed with a continuous curved surface on which a surface acoustic wave propagates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a $Bi_{12}SiO_{20}$ crystal, and, along the surface of the three-dimensional substrate, the electro-acoustic transducing element propagates the excited surface acoustic wave along a line of intersection between a crystal face of the $Bi_{12}SiO_{20}$ crystal and the surface thereof, the line of intersection defined as an outermost circumferential line of the surface.

In order to achieve the above described object, another surface acoustic wave device according to this invention comprises:

a three-dimensional substrate having a surface, which includes at least a part of an annular curved surface formed with a continuous curved surface on which a surface acoustic wave progapates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a $Li_2B_4O_7$ crystal, and, along the surface of the three-dimensional substrate, the electro-acoustic transducing element propagates the excited surface acoustic wave along a line of intersection between a crystal face of the $Li_2B_4O_7$ crystal and the surface thereof, a normal line of the crystal face extending in a direction orthogonal to a C crystal axis of the $Li_2B_4O_7$ crystal, and the line of intersection defined as an outermost circumferential line of the surface.

In order to achieve the above described object, a further surface acoustic wave device according to this invention comprises:

a three-dimensional substrate having a surface, which includes at least a part of an annular curved surface formed with a continuous curved surface on which a surface acoustic wave propagates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a $Li_2B_4O_7$ crystal, and, along the surface of the three-dimensional substrate, the electro-acoustic transducing element propagates the excited surface acoustic wave along a line of intersection between a crystal face of the $Li_2B_4O_7$ crystal and the surface thereof, the normal line of the crystal face extending in a direction inclined between 30° and 40° in an arbitrary direction from a C crystal axis of the $Li_2B_4O_7$ crystal, and the line of intersection defined as an outermost circumferential line of the surface.

In order to achieve the above described object, a more further surface acoustic wave device according to this invention comprises:

a three-dimensional substrate having a surface, which includes at least a part of an annular curved surface formed with a continuous curved surface on which a surface acoustic wave propagates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a $LiNbO_3$ crystal, and, along the surface of the three-dimensional substrate, the electro-acoustic transducing element propagates the excited surface acoustic wave along at least one of two lines of intersections, one of which is defined between one crystal face of the $LiNbO_3$ crystal and the surface thereof, a normal line of the one crystal face being a crystal axis specified by rotating a +Y axis that is a crystal axis of the $LiNbO_3$ crystal by 20° in a +Z direction with an X axis being a rotational center, and the other of which is defined between the other crystal face of the $LiNbO_3$ crystal and the surface thereof, a normal line of the other crystal face being a crystal axis specified by rotating a +Y axis that is a crystal axis of the $LiNbO_3$ crystal by 26° in a −Z direction with an X axis being a rotational center, and the at least one of the two lines of intersections defined as an outermost circumferential line.

In order to achieve the above described object, a more further surface acoustic wave device according to this invention comprises:

a three-dimensional substrate having a surface, which includes at least a part of an annular curved surface formed with a continuous curved surface on which a surface acoustic wave propagates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a $LiTaO_3$ crystal, and, along the surface of the three-dimensional substrate, the electro-acoustic transducing element propagates the excited surface acoustic wave along a line of intersection between a crystal face of the $LiTaO_3$ crystal and the surface thereof, a normal line of the crystal face being a crystal axis specified by rotating a +Y axis that is a crystal axis of the $LiTaO_3$ crystal by 45° in a −Z direction with an X axis being a rotational center, and the line of intersection defined as an outermost circumferential line.

In order to achieve the above described object, a more further surface acoustic wave device according to this invention comprises:

a three-dimensional substrate having a surface, which includes at least a part of an annular curved surface formed with a continuous curved surface on which a surface acoustic wave propagates; and an electro-acoustic transducing element, which excites the surface acoustic wave along the surface, which propagates the surface acoustic wave along the surface, and which receives the surface acoustic wave propagating along the surface, the device characterized in that the three-dimensional substrate is made of a quartz crystal, and, along the surface of the three-dimensional substrate, the electro-acoustic transducing element propagates the excited surface acoustic wave along a line of intersection between a crystal face of the quartz crystal and the surface thereof, a normal line of the crystal face being a Y axis that is a crystal axis of the quartz crystal, and the line of intersection defined as an outermost circumferential line.

In order to achieve the above described object, an environmental difference detecting apparatus according to this invention is characterized in that:

along the surface of each of the above described surface acoustic wave devices according to this invention, a plurality of electro-acoustic transducing elements excite surface acoustic waves, propagate the surface acoustic waves along a plurality of lines of intersection of the surface of the surface acoustic wave device, and receive the propagated surface acoustic waves to output reception signals;

the reception signals outputted from the plurality of electro-acoustic transducing elements are compared with each other; and an environmental difference in a plurality of portions of a space, with which the plurality of portions along the surface propagating the plurality of surface acoustic waves come into contact, is detected.

In the present invention, a pseudo surface acoustic wave or, for example, a corridor wave, which is excited by an electro-acoustic transducing element immediately beneath a surface of a crystalline material forming the three-dimensional substrate, and which is propagated in the immediately beneath the surface, is referred to as a surface acoustic wave. Further, as is, for example, a boundary acoustic wave, even an acoustic wave which propagates along a surface of a three-dimensional substrate on which a different substance adhering the surface and which is not referred to as a surface acoustic wave in general, is referred to as a surface acoustic wave herein.

Even if any film is formed on a portion of a surface of a three-dimensional substrate along which a surface acoustic wave propagates, or even if an electro-acoustic transducing element is formed on the surface with any film being sandwiched therebetween, the presence of such a film is permitted as long as such a film does not substantially inhibit a desired propagation of a surface acoustic wave.

Further, in the CLAIMS, DESCRIPTION, and accompanying DRAWINGS of the present application, the crystal axes of the $LiNbO_2$ crystal, the $LiTaO_3$ crystal, and the quartz crystal of the three-dimensional substrate are expressed by the signs of + and − or X, Y, and Z axes. Such an expression is a conventionally known expressing method relating to a crystal axis of a piezoelectric crystal.

In the above-described surface acoustic device according to the invention and in the above-described environmental difference detecting apparatus according to the invention and using the surface acoustic wave device according to the invention, the three-dimensional substrate having the surface capable of propagating the surface acoustic wave is formed of the $Bi_{12}SiO_{20}$ crystal or the $Li_2B_4O_7$ crystal. Moreover, along the surface of each of the crystals, the surface acoustic wave excited along the surface by the electro-acoustic transducing element is propagated along the line of intersection between the specific crystal face of each of the crystals and the surface thereof, and the line of intersection is defined as the outermost circumferential line of the surface. Consequently, it is possible to easily mass-produce the surface acoustic wave device at a low cost, and also to make the surface acoustic wave device achieve consistently a good surface acoustic wave propagating performance.

In the above-described surface acoustic device according to the invention and in the above-described environmental difference detecting apparatus according to the invention and using the surface acoustic wave device according to the invention, the three-dimensional substrate having the surface capable of propagating the surface acoustic wave is formed of the $LiNbO_3$ crystal, the $LiTaO_3$ crystal, or the quartz crystal. Moreover, along the surface of each of the crystals, the surface acoustic wave excited along the surface by the electro-acoustic transducing element is propagated along the line of intersection between the specific crystal face of each of the crystals and the surface thereof, and the line of intersection is defined as the outermost circumferential line of the surface. Consequently, it is possible to easily mass-produce the surface acoustic wave device at a low cost, and also to make the surface acoustic wave device achieve consistently a good surface acoustic wave propagating performance.

In order to restrict a generation of noise during a production process of the surface acoustic device or during a use thereof due to pyroelectricity with respect to the three-dimensional substrate formed of each of the $LiNbO_3$ crystal and the $LiTaO_3$ crystal, conductivity of the three-dimensional substrate formed of each of the $LiNbO_3$ crystal and the $LiTaO_3$ crystal can be controlled by applying a surface treatment thereto.

In the above-described surface acoustic device according to the invention and in the above-described environmental difference detecting apparatus according to the invention and using the surface acoustic wave device according to the invention, each of the $LiNbO_3$ crystal and the $LiTaO_3$ crystal, whose composition ratio has been changed and which are applied with a variety of treatment for controlling a variety of physical properties, such as a black lithium niobate and black lithium tantalite obtained by applying, for example, the above described surface treatment, is not excluded.

Further, the present invention does not exclude such a crystal, which is each of the $LiNbO_3$ crystal and $LiTaO_3$ crystal each added with, for example, magnesium in their crystallization process, or which is each of the above-described $Bi_{12}SiO_{20}$ crystal, $Li_2B_4O_7$ crystal, $LiNbO_3$ crystal and $LiTaO_3$ crystal each changed in composition ratio or added with other element in a range of no changing in crystalline system thereof and no losing piezoelectric characteristics thereof.

The "transmitting and receiving portion" which is described in the present invention, for exciting and receiving the surface acoustic wave along the surface of the three-dimensional substrate, can also be configured as two mutually independent portions obtained by dividing the transmitting and receiving portion in its function into a "transmitting portion" and a "receiving portion". Where the "transmitting portion" and the "receiving portion" are configured as mutually independent portions, designs of a drive circuit and a detector circuit for these portions are easily made. However, in a case where a surface acoustic wave circulates along the surface many times, the surface acoustic wave passes through the mutually independent "transmitting portion" and "receiving portion" at every circulation. Thus, the propagation efficiency of the surface acoustic wave is slightly lowered as compared with a case in which the "transmitting portion" and the "receiving portion" are not configured as mutually independent portions, but no practical problem occurs.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a view schematically showing a further preferred arrangement of an electro-acoustic transducing element using a ladder shaped electrode with respect to the outermost circumferential line corresponding thereto in the band shaped propagating surface zone of the three-dimensional substrate of the surface acoustic wave device according to the first embodiment of the invention.

FIG. 6 is a perspective view schematically showing a surface acoustic wave device according to a second embodiment of the present invention.

FIG. 12 is a perspective view schematically showing, in a case where a whole three-dimensional substrate of the surface acoustic wave device according to the sixth embodiment of the invention is formed of a $LiNbO_3$ crystal, how to define an outermost circumferential line serving as a reference of a band shaped zone for propagating a surface acoustic wave along an outer surface of the three-dimensional substrate, along one of three crystal faces of the $LiNbO_3$ crystal.

FIG. 13 is a schematic view in which the three-dimensional substrate of FIG. 12 is seen from a +Z direction side toward a −Z direction side in order to show three outermost circumferential lines serving as references for three band shaped propagating surface zones set along the outer surface of the three-dimensional substrate as shown in FIG. 12.

FIG. 14 is a perspective view schematically showing, in the case where the whole three-dimensional substrate of the surface acoustic wave device according to the sixth embodiment of the invention is formed of the $LiNbO_3$ crystal, how to define an outermost circumferential line serving as a reference of a band shaped zone for propagating a surface acoustic wave along an outer surface of the three-dimensional substrate, along one of other three crystal faces of the $LiNbO_3$ crystal.

FIG. 15 is a schematic view in which the three-dimensional substrate of FIG. 14 is seen from a +Z direction side toward a −Z direction side in order to show three outermost circumferential lines serving as references for other three band shaped propagating surface zones set along the outer surface of the three-dimensional substrate as shown in FIG. 14.

FIG. 16 is a view schematically showing a preferred arrangement of an electro-acoustic transducing element with respect to the outermost circumferential line corresponding thereto in the band shaped propagating surface zone of the three-dimensional substrate of the surface acoustic wave device according to the sixth embodiment of the invention.

FIG. 17 is a view schematically showing a further preferred arrangement of an electro-acoustic transducing element using a ladder shaped electrode with respect to the outermost circumferential line corresponding thereto in the band shaped propagating surface zone of the three-dimensional substrate of the surface acoustic wave device according to the sixth embodiment of the invention.

FIG. 20 is a perspective view schematically showing, in a case where a whole three-dimensional substrate of the surface acoustic wave device according to a second modification of the sixth embodiment of the invention is formed of a quartz crystal, how to define an outermost circumferential line serving as a reference of a band shaped zone for propagating a surface acoustic wave along an outer surface of the three-dimensional substrate, along one of three crystal faces of the quartz crystal.

FIG. 21 is a schematic view in which the three-dimensional substrate of FIG. 20 is seen from a +Z direction side toward a −Z direction side in order to show three outermost circumferential lines serving as references for three band shaped propagating surface zones set along the outer surface of the three-dimensional substrate as shown in FIG. 20.

DETAILED DESCRIPTION OF THE INVENTION

First Embodiment

Hereinafter, a first embodiment of a surface acoustic wave device according to the present invention will be described in detail with reference to FIGS. 1 to 3 in the accompanying drawings.

Figure 1:
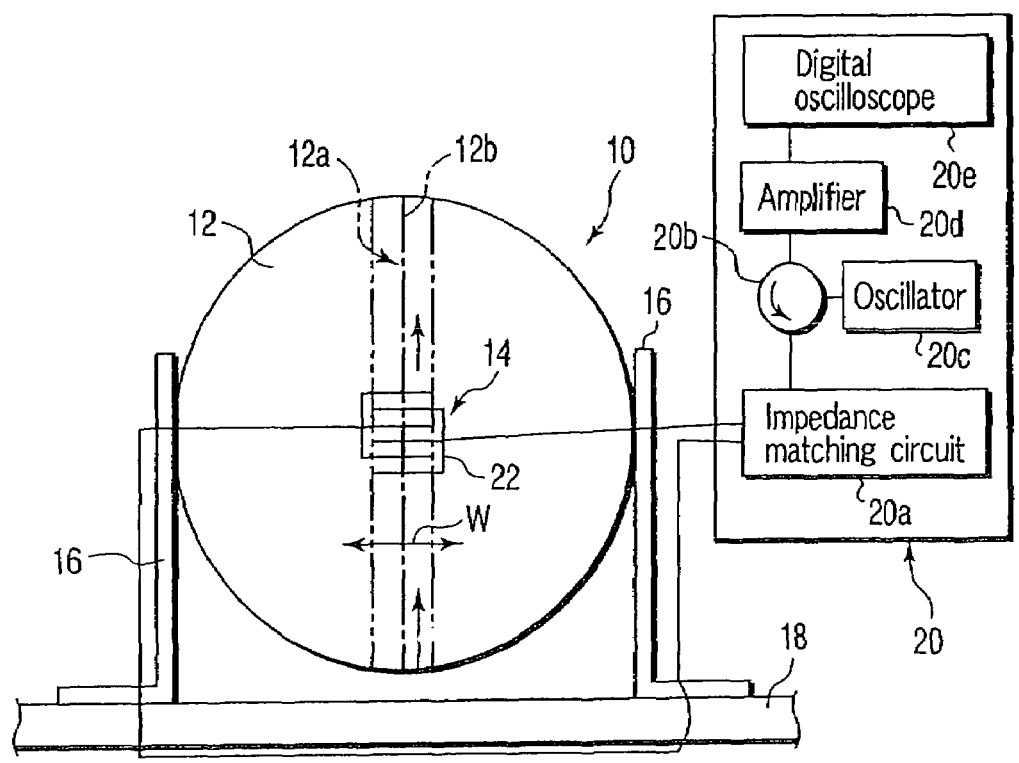
FIG. 1 is a schematic view of a surface acoustic wave device according to a first embodiment of the present invention.

FIG. 1 shows an appearance of a surface acoustic wave device 10 according to the first embodiment. The surface acoustic wave device 10 comprises: a three-dimensional substrate 12 having a surface, which includes a band shaped propagating surface zone 12a formed of at least a part of a continuous annular curved surface on which a surface acoustic wave propagates; and an electro-acoustic transducing element 14, which excites the surface acoustic wave along the band shaped propagating surface zone 12a, which propagates the surface acoustic wave along the band shaped propagating surface zone 12a, and which receives the surface acoustic wave propagating along the band shaped propagating surface zone 12a.

Here, the band shaped propagating surface zone 12a is drawn such that a dimension in its widthwise direction W is uniform at any points in a direction in which the band shaped propagating surface zone 12a is continuous in the annular shape, in order to simplify the drawing of FIG. 1. However, actually, while the surface acoustic wave propagates in the direction in which the band shaped propagating surface zone 12a is continuous in the annular shape along the surface of the three-dimensional substrate 12, the dimension of the surface acoustic wave in the widthwise direction W may be uniform as shown in FIG. 1 or may repeatedly diverge and converge.

In any case, it is practically desired that the surface acoustic wave propagates along the band shaped propagating surface zone 12a for a desired distance from the electro-acoustic transducing element 14 or per one circulation, while keeping at least 80% or more of energy thereof.

In this embodiment, whole of the three-dimensional substrate 12 is formed of a $Li_2B_4O_7$ crystal in a spherical shape. Therefore, in this embodiment, the band shaped propagating surface zone 12a is continuous in the annular shape along the spherically shaped surface of the three-dimensional substrate 12. The band shaped propagating surface zone 12a is continuous along an outermost circumferential line 12b of the three-dimensional substrate 12, and preferably, the outermost circumferential line 12b is included in the range of the band shaped propagating surface zone 12a.

Figure 2:
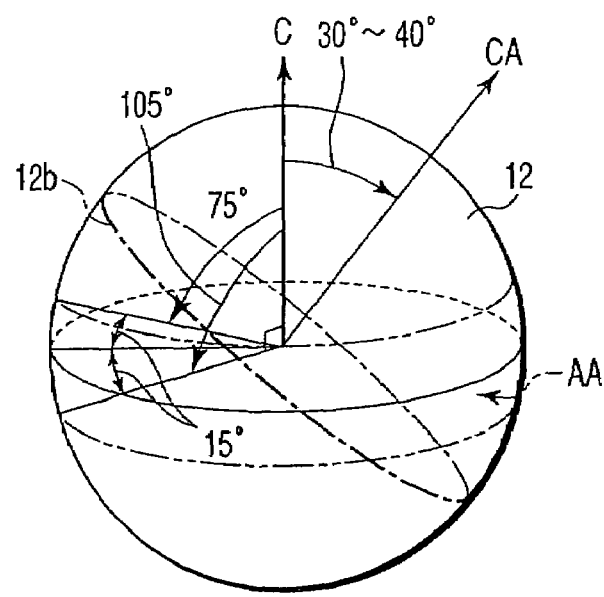
FIG. 2 is a perspective view schematically showing, in a case where a whole three-dimensional substrate of the surface acoustic wave device according to the first embodiment of the invention is formed of a $Li_2B_4O_7$ crystal, how to define an outermost circumferential line serving as a reference of a band shaped zone for propagating a surface acoustic wave along an outer surface of the three-dimensional substrate, along one in a group of crystal faces of the $Li_2B_4O_7$ crystal, and further schematically showing a preferred band shaped area for arranging an electro-acoustic transducing element.

On the outer surface of the three-dimensional substrate 12, the outermost circumferential line 12b, as shown in FIG. 2, coincides with a line of intersection between one crystal face of the $Li_2B_4O_7$ crystal and the outer surface of the three-dimensional substrate 12, a normal line of the crystal face extending in a direction CA inclined between 30° and 40° in an arbitrary direction from a C crystal axis of the $Li_2B_4O_7$ crystal (wherein the above described arbitrary direction is an arbitrary angle direction in a whole circumference of 360° around the C crystal axis). That is, the outermost circumferential line 12b along which the band shaped propagating surface zone 12a extends along one crystal face of the $Li_2B_4O_7$ crystal on the outer surface of the three-dimensional substrate 12. While the surface acoustic wave propagates along the above described crystal face on the outer surface of the three-dimensional substrate 12, a large energy diffusion of the surface acoustic wave, which is generated in a case where the surface acoustic wave propagates along the outer surface to cross the above crystal face, will not occur. Thus, the surface acoustic wave can propagate most efficiently along the outer surface of the three-dimensional substrate 12.

On the outer surface of the three-dimensional substrate 12 according to the first embodiment, whole of which is formed of the $Li_2B_4O_7$ crystal, the outermost circumferential line 12b, along which the band shaped propagating surface zone 12a is continuous, can be specified as follows.

Figure 3:
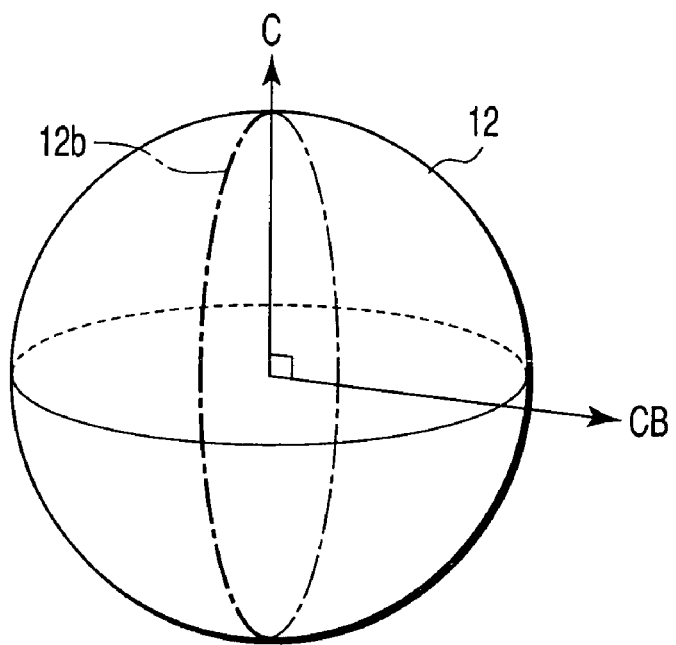
FIG. 3 is a perspective view schematically showing, in the case where the whole three-dimensional substrate of the surface acoustic wave device according to the first embodiment of the invention is formed of the $Li_2B_4O_7$ crystal, how to define the outermost circumferential line serving as the reference of the band shaped zone for propagating the surface acoustic wave along the outer surface of the three-dimensional substrate, along one in another group of crystal faces of the $Li_2B_4O_7$ crystal.

That is, on the outer surface of the three-dimensional substrate 12, the outermost circumferential line 12b, as shown in FIG. 3, is aligned with a line of intersection between other crystal face of the $Li_2B_4O_7$ crystal and the outer surface of the three-dimensional substrate 12, a normal line of the other crystal face extending in a direction CB, which is orthogonal to the C crystal axis of the $Li_2B_4O_7$ crystal. This means that the outermost circumferential line 12b on the outer surface of the three-dimensional substrate 12, along which the band shaped propagating surface zone 12a extends along a crystal face specified independently of the crystal face, the normal line of which extends in the direction CA inclined between 30° and 40° in the arbitrary direction from the C crystal axis of the $Li_2B_4O_7$ crystal (wherein the above described arbitrary direction is the arbitrary angle direction in the whole circumference of 360° around the C crystal axis). While the surface acoustic wave propagates along the above described other specified crystal face on the outer surface of the three-dimensional substrate 12, a large energy diffusion of the surface acoustic wave will not occur in a direction orthogonal to the above described other specified crystal face, as in the case of the crystal face described with reference to FIG. 2. Thus, the surface acoustic wave can propagate most efficiently along the outer surface of the three-dimensional substrate 12.

In addition, it is possible to visually estimate an actual width of the surface acoustic wave, which propagates along the surface of the three-dimensional substrate 12, in a direction orthogonal to its propagating direction along the surface, because, for example, after depositing water droplets on the surface, the surface acoustic wave does not propagate along a portion of the surface on which water droplets are deposited.

In general, in a case where a surface acoustic wave having a high frequency is excited by using a ladder shaped electrode as an electro-acoustic transducing element, an effective width of the ladder shaped electrode (that is, a dimension of a portion of the ladder shaped electrode, at that portion the ladder shaped electrode excites a surface acoustic wave along the surface of the three-dimensional substrate and propagates the excited wave in a desired direction and receives the surface acoustic wave propagating along the surface, in a direction orthogonal to the desired direction along the surface) is reduced. However, it is found that a surface acoustic wave exciting and receiving efficiency of the effective width of the ladder shaped electrode is extremely lowered where the effective width is greater than 1.5 times of a radius of curvature of a band shaped propagating surface zone (designated by reference numeral 12a in FIG. 1) on the outer surface in a direction, which is the above desired direction, orthogonal to an outermost circumferential line (designated by reference numeral 12b in FIG. 1).

Portions of the outer surface of the three-dimensional substrate 12, which are other than the propagating surface zone 12a along which the surface acoustic wave excited by the electro-acoustic transducing element 14 propagates, are supported on a base 18 by supporting arms 16. In order to have no effect on the surface acoustic wave propagating along the propagating surface zone 12a, nothing but the electro-acoustic transducing element 14 is brought into contact with the propagating surface zone 12a. Therefore, in the present embodiment, an electro-acoustic transducing element control unit 20, which makes the electro-acoustic transducing element 14 excite the surface acoustic wave along the propagating surface zone 12a and receives a signal from the electro-acoustic transducing element 14 when the electro-acoustic transducing element 14 receives the surface acoustic wave propagating along the propagating surface zone 12a, is connected to the electro-acoustic transducing element 14 by lead wires extending from the electro-acoustic transducing element 14 on the portions of the outer surface of the three-dimensional substrate 12 other than the propagating surface zone 12a. The electro-acoustic transducing element control unit 20 comprises, for example, an impedance matching circuit 20a, a circulator 20b, an oscillator 20c including a high frequency power supply, an amplifier 20d, and a digital oscilloscope 20e, etc. as shown in FIG. 1. A high frequency radio wave receiving antenna can also be used instead of the oscillator 20c.

Figure 4:
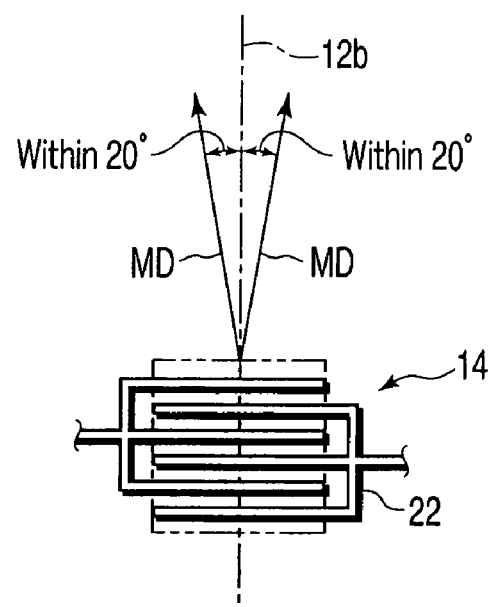
FIG. 4 is a view schematically showing a preferred arrangement of an electro-acoustic transducing element with respect to the outermost circumferential line corresponding thereto in the band shaped propagating surface zone of the three-dimensional substrate of the surface acoustic wave device according to the first embodiment of the invention.

As shown in FIG. 4, it is preferable that the electro-acoustic transducing element 14 is configured so that an orientation MD, in which a flow density of energy of a surface acoustic wave excited along the propagating surface zone 12a becomes maximum, is within 20° with respect to the outermost circumferential line 12b. This angle is more preferably within 10°, and further preferably within 5°. This means that, as long as the surface acoustic wave excited along the propagating surface zone 12a by the electro-surface transducing element 14 can circulate at a small attenuation rate such that, for example, 80% or more of energy can be maintained every circulation along the outermost circumferential line 12b on the outer surface of the three-dimensional substrate 12, the surface acoustic wave may be diffused from the outermost circumferential line 12b more than a width of the surface acoustic wave immediately after it is excited, while the surface acoustic wave propagates, but it is preferable that the surface acoustic wave is excited by the electro-surface transducing element 14 such that the orientation MD is within the above described angles.

A phrase "along the outermost circumferential line" described with respect to the present invention means a case in which, when the surface acoustic wave circulates or propagates along a propagation passage, a direction, in which the flow density of energy of the surface acoustic wave becomes maximum, is preferably within 20°, more preferably within 10°, and further preferably within 5° with respect to the outermost circumferential line.

In this embodiment, the electro-acoustic transducing element 14 is directly formed on the outer surface of the three-dimensional substrate 12 within the propagating surface zone 12a. In this embodiment, the electro-acoustic transducing element 14 is a ladder shaped electrode 22 such as, for example, a comb shaped electrode, and can be directly formed on the outer surface with a variety of publicly known processes such as, for example, vapor deposition, printing, sputtering, and sol-gel techniques.

In the case where the electro-acoustic transducing element 14 is formed of the ladder shaped electrode 22, it is preferable that, as well shown in FIG. 5, the ladder shaped electrode 22 is configured so that a line extending along the outer surface of the three-dimensional substrate 12 and being orthogonal to a transmitting and receiving portion (a portion of the above described effective width) of the ladder shaped electrode 22 capable of exciting a surface acoustic wave along the propagating surface zone 12a and receiving the surface acoustic wave propagating along the propagating surface zone 12a, is included in a range equal to or smaller than 10° with respect to the outermost circumferential line 12b, along which the propagating surface zone 12a extends. In more detail, this means that it is preferable that an orthogonal line OL, which extends along the outer surface of the propagating surface zone 12a and which is orthogonal to the transmitting and receiving portion at each terminal (line element) 22a in the pattern of the ladder shaped electrode 22 [in the case of the ladder shaped electrode 22, the transmitting and receiving portion at each terminal (line element) 22a in the pattern of the ladder shaped electrode 22, overlapping each other in a direction along the outermost circumferential line 12b], is in a range equal to or smaller than 10° with respect to the outermost circumferential line 12b.

The reason is identical to the reason why it is preferable that the electro-acoustic transducing element 14 is configured so that the orientation MD, in which the flow density of energy of the surface acoustic wave excited along the propagating surface zone 12a becomes maximum, is within 20° with respect to the outermost circumferential line 12b, as described previously with reference to FIG. 4.

Further, it is preferable that an arrangement pitch P of the plurality of terminals 22a (see FIG. 5) in the pattern of the ladder shaped electrode 22 in a direction along the outermost circumferential line 12b is equal to or smaller than 1/10 of the radius of curvature of the outermost circumferential line 12b. The arrangement pitch P is equivalent to one wavelength (i.e., vibration cycle) of the surface acoustic wave excited by the ladder shaped electrode 22.

When the wavelength of the surface acoustic wave (i.e., the arrangement pitch P of the plurality of terminals 22a in the pattern of the ladder shaped electrode 22) is greater than 1/10 of the radius of curvature of the outermost circumferential line 12b included in the propagating surface zone 12a along which the surface acoustic wave propagates (in the case where the propagating surface zone 12a is a part of the spherical surface as in this embodiment, the radius of curvature is a radius of the spherical surface), a function of a geometrical feature of the curved propagating surface zone 12a to restrict diffusion of the surface acoustic wave propagating along the propagating surface zone 12a becomes weak. Therefore, in order to propagate a surface acoustic wave having a comparatively long wavelength along the propagating surface zone 12a on the surface of the three-dimensional substrate 12 for a desired distance, the radius of curvature of the outermost circumferential line 12b included in the propagation surface zone 12a must be preset so as to meet the above-described relationship with the above wavelength.

Consequently, it is preferable that the arrangement pitch is defined as described above to efficiently propagate a surface acoustic wave along the propagating surface zone 12b.

Further, in the case where the three-dimensional substrate 12 is formed of the $Li_2B_4O_7$ crystal as described above, it is found to be preferable that the transmitting and receiving portion of the electro-acoustic transducing element 14, which is capable of exciting a surface acoustic wave along the outer surface of the three-dimensional substrate 12, propagating the surface acoustic wave along the surface, and receiving the surface acoustic wave propagating along the outer surface, is arranged so as to include a part of the line of intersection (outermost circumferential line 12b) on the outer surface of the three-dimensional substrate 12. With such an arrangement, an efficiency of the transmitting and receiving portion of the electro-acoustic transducing element 14 to excite and receive the surface acoustic wave can be improved more remarkably.

In addition to such an arrangement, in the case where the three-dimensional substrate 12 is formed of the $Li_2B_4O_7$ crystal as described above, and the outermost circumferential line 12b is specified as shown in FIG. 2, it is found to be further preferable that, in order to improve the above-described efficiency of the transmitting and receiving portion of the electro-acoustic transducing element 14 more remarkably, the transmitting and receiving portion of the electro-acoustic transducing element 14 is arranged in a band shaped area AA, which is defined between 75° and 105° in an arbitrary direction from the C axis described above, on the outer surface of the three-dimensional substrate 12.

When the spherically shaped three-dimensional substrate 12 is presumed as the earth, the C axis is equivalent to the earth's axis of the earth, and the outermost circumferential line 12b specified as shown in FIG. 3 is equivalent to the longitude line on the earth. In addition, the band shaped area AA specified as shown in FIG. 2 is equivalent to a band shaped portion that is sandwiched between latitude 150 north and latitude 150 south and that continuously extends in an annular shape along the equator.

In FIG. 2, only a portion of the band shaped area AA which can be seen on the outer surface of the three-dimensional substrate 12 is shown in order to avoid complication of the figure. However, in actuality, the band shaped area AA continuously extends even in a portion of the outer surface of the three-dimensional substrate 12, which cannot be seen on the outer surface of the three-dimensional substrate 12, and forms an annular shape.

First Modification of First Embodiment

Now, a first modification of the first embodiment of the surface acoustic wave device according to the present invention will be described in detail.

In a surface acoustic wave device of this modification, the three-dimensional substrate 12, which is formed of the $Li_2B_4O_7$ in the first embodiment, is formed of a $Bi_{12}SiO_{20}$ crystal in a spherical shape. Concurrently, a method for specifying the outermost circumferential line 12b on the outer surface of the three-dimensional substrate 12 is also different from that in the case of the three-dimensional substrate 12 formed of the $Li_2B_4O_7$ in the first embodiment described previously. However, structural elements other than those described above are identical to those of the surface acoustic device of the first embodiment described previously.

In the surface acoustic wave device of this modification, the outermost circumferential line 12b on the outer surface of the three-dimensional substrate 12 formed of the $Bi_{12}SiO_{20}$ crystal is aligned with a line of intersection between a crystal face (111) of the $Bi_{12}SiO_{20}$ crystal and the outer surface of the three-dimensional substrate 12. Also, while a surface acoustic wave propagates along such one crystal face along the outer surface of the three-dimensional substrate 12, significant diffusion of energy of the surface acoustic wave does not occur in a direction intersecting with the above-described crystal face, as is the case with the crystal face of the first embodiment described previously. Thus, it is possible to most efficiently propagate the surface acoustic wave along the outer surface of the three-dimensional substrate 12.

Second Embodiment

Now, a second embodiment of the surface acoustic wave device according to the present invention will be described in detail with reference to FIG. 6.

In a surface acoustic wave device 30 of this embodiment, electro-acoustic transducing elements 14 are formed as described above along portions on an arbitrary plurality of propagating surface zones 12a that can be specified as described above on the outer surface of the three-dimensional substrate 12 of the surface acoustic wave device 10 according to the above-described first embodiment or the modification thereof, that portions on the arbitrary plurality of propagating surface zones 12a not intersecting with other propagating surface zone 12a. And, each of the electro-acoustic transducing elements 14 is connected to the electro-acoustic element control unit 20 described above.

In FIG. 6, only portions of the band shaped zones 12a which can be seen on the outer surface of the three-dimensional substrate 12 are shown in order to avoid complication of the figure. However, in actuality, the band shaped zones 12a continuously extend even in a portion of the outer surface of the three-dimensional substrate 12, which cannot be seen on the outer surface of the three-dimensional substrate 12, and each band shaped zone 12a forms an annular shape.

Herein, in the case where the three-dimensional substrate 12 is formed of the $Li_2B_4O_7$ crystal as described above, it is preferable that transmitting and receiving portion of the electro-acoustic transducing element 14, which is capable of exciting a surface acoustic wave along the outer surface of the three-dimensional substrate 12 and propagating the surface acoustic wave along the outer surface and receiving the surface acoustic wave propagating along the outer surface, is arranged so as to include a part of the line of intersection (outermost circumferential line 12b) on the outer surface of the three-dimensional substrate 12. Such an arrangement of the transmitting and receiving portion of the electro-acoustic transducing element 14 can improve the surface acoustic more remarkably.

In addition to such an arrangement, in the case where the three-dimensional substrate 12 is formed of the $Li_2B_4O_7$ crystal as described above and the outermost circumferential line 12b is specified as shown in FIG. 2, it is further preferable that the transmitting and receiving portion of the electro-acoustic transducing element 14 is arranged in the band shaped area AA between 75° and 105° from the C axis in the arbitrary direction as described above in order to improve the above-described efficiency of the transmitting and receiving portion of the electro-acoustic transducing element 14 more remarkably.

Further, in this embodiment, a support member 32 for supporting the three-dimensional substrate 12 on any base (not shown) is fixed at a position on the outer surface of the three-dimensional substrate 12 excluding a plurality of propagating surface zones 12a and the band shaped area AA, in which the electro-acoustic transducing elements 14 are formed.

The surface acoustic wave device 30 according to the second embodiment and configured as described above is more excellent when it is used as an environmental difference detecting apparatus, as compared with the surface acoustic wave device 10 according to each of the first embodiment and the modification thereof. The reason is as follows.

In the case that one electro-acoustic transducing element 14 and one electro-acoustic transducing element control unit 20 connected thereto are used as in the surface acoustic wave device 10 described above, when any physical change (for example, expansion or contraction of the three-dimensional substrate 12 due to a temperature change in an external environment) occurs in the surface acoustic wave device 10 due to an effect of a change in the external environment described above, a slight change occurs in a propagation speed of the surface acoustic wave propagating along the propagating surface zone 12a or in a propagation time required for one circulation.

Therefore, in order to detect more precisely a change of a fluid (gas or liquid) filled in a space, with which the propagating surface zone 12a comes into contact (i.e., change in external environment, with which the propagating surface zone 12a comes into contact), a physical change of the surface acoustic wave device 10 due to an effect of the change in the external environment described above must be considered.

The surface acoustic wave device 30 of the second embodiment described with reference to FIG. 6 is configured so that at least one of the plurality of propagating surface zones 12a, along which the electro-acoustic transducing elements 14 are formed, on the outer surface of the three-dimensional substrate 12 is isolated from an external environment in which a change is to be detected, and that at least another of the plurality of propagating surface zones 12a, along which the electro-acoustic transducing elements 14 are formed, is brought into contact with the external environment.

With such a configuration, a signal, which is received from the electro-acoustic transducing element 14 along the propagating surface zone 12a isolated from the external environment by the above described electro-acoustic transducing element control unit 20 corresponding to the transducing element along the isolated propagating surface zone, indicates a physical change of the surface acoustic wave device 10 due to the change in the external environment. In addition, a signal, which is received from the electro-acoustic transducing element 14 along another propagating surface zone 12a being in contact with the external environment by the above described electro-acoustic transducing element control unit 20 corresponding to the transducing element along the contacted propagating surface zone, indicates a change in external environment, together with the physical change of the surface acoustic wave device 10 due to the change in external environment.

Therefore, by subtracting the signal, which is received from the electro-acoustic transducing element 14 along the propagating surface zone 12a isolated from the external environment by the electro-acoustic transducing element control unit 20 corresponding to the electro-acoustic transducing element along the isolated propagating surface zone, from the signal, which is received from the electro-acoustic transducing element 14 along another propagating surface zone 12a being in contact with the external environment by the electro-acoustic transducing element control unit 20 corresponding to the electro-acoustic transducing element along the contacted propagating surface zone, it possible to detect only a pure change in the external environment.

Third Embodiment

Figure 7:
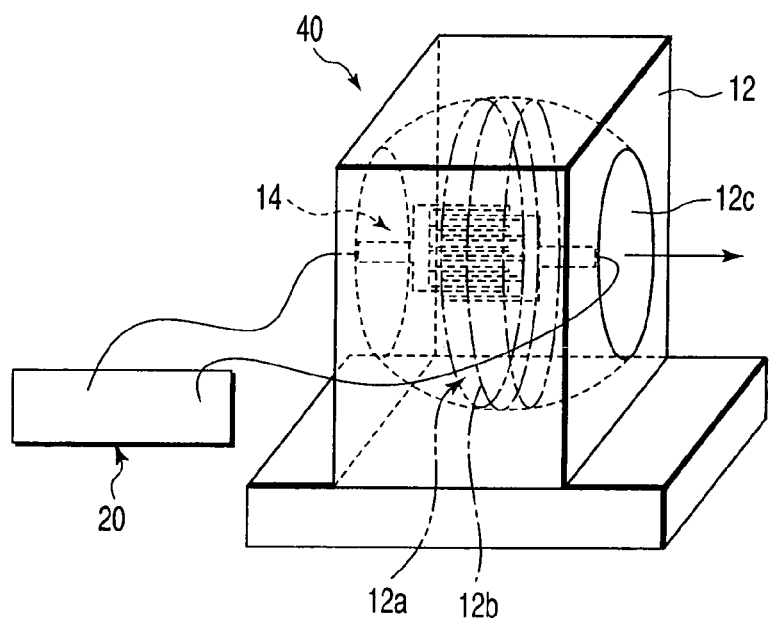
FIG. 7 is a perspective view schematically showing a surface acoustic wave device according to a third embodiment of the present invention.

Now, a third embodiment of the surface acoustic wave device according to the present invention will be described in detail with reference to FIG. 7.

In a surface acoustic wave device 40 according to the third embodiment, the three-dimensional substrate 12 has a recessed portion or hollow portion, and the recessed portion or an inner surface 12c of the hollow portion includes the propagating surface zone 12a, along which a surface acoustic wave can propagate and which is a curved surface continuous in an annular shape. FIG. 7 shows the three-dimensional substrate 12 having a through hole that is a kind of the hollow portion.

The whole of three-dimensional substrate 12 is formed of a $Li_2B_4O_7$ crystal or $Bi_{12}SiO_{20}$ crystal as in the three-dimensional substrate 12 according to the above-described first embodiment or its modification. In addition, at least one outermost circumferential line 12b, which becomes a reference along which the band shaped propagating surface zone 12a extends, is specified on the inner surface of the three-dimensional substrate 12 of the surface acoustic wave device 40 according to the third embodiment, along a line of intersection between at least one of a plurality of crystal faces specific to the crystal forming the three-dimensional substrate 12 and the inner surface thereof, in the same manner as in the case where the outermost circumferential line 12b is specified on the outer surface of the three-dimensional substrate 12 according to the above-described first embodiment and its modification, the outermost circumferential line 12b serving as the reference for the propagating surface zone 12a along the line of intersection between at least one of the plurality of crystal faces specific to the crystal forming the three-dimensional substrate 12 and the outer surface thereof. And, the propagating surface zone 12a is specified so as to extend continuously along the outermost circumferential line 12b on the inner surface. A method for specifying the propagating surface zone 12a along the inner surface of the three-dimensional substrate 12 according to the present embodiment is identical to that for specifying the propagating surface zone 12a along the outer surface of the three-dimensional substrate 12 according to the above-described first embodiment and its modification. Therefore, the outermost circumferential line 12b is preferably included in the range of the propagating surface zone 12a along the inner surface.

And, in the propagating surface zone 12a along the inner surface of the three-dimensional substrate 12 of this embodiment, the electro-acoustic transducing element 14 is formed so as to propagate the surface acoustic wave along the outermost circumferential line 12b in the range of the propagating surface zone 12a without significantly attenuating it, and the above described electro-acoustic transducing element control unit 20 is connected to the electro-acoustic transducing element 14.

Also, in this embodiment, a portion of the inner surface other than the propagating surface zone 12a may be formed in an arbitrary shape as long as the propagating surface zone 12a is specified in accordance with the above described predetermined method.

In this embodiment, the acoustic surface wave, which is excited along the propagating surface zone 12a by the electro-acoustic transducing element 14 and which propagates along the propagating surface zone 12a while keeping its energy of, for example, 80% or more per one circulation without significant attenuation, changes in response to a variety of changes in a fluid (gas or liquid) passing through the internal space of a through hole that is an environment, with which the propagating surface zone 12a along the inner surface of the three-dimensional substrate 12 comes into contact. And, the surface acoustic wave device 40 of the present embodiment can detect a change in the environment, i.e., a difference in the environment, by receiving the change in the signal, which is generated from the electro-acoustic transducing element 14, in the electro-acoustic transducing element control unit 20.

Further, in this embodiment, as in the surface acoustic wave device 30 of the second embodiment described above with reference to FIG. 6, a plurality of electro-acoustic transducing elements 14, each of which is connected to the electro-acoustic transducing element control unit 20, can be formed along a plurality of propagating surface zones 12a along a plurality of outermost circumferential lines 12b aligned with a plurality of lines of intersection between a plurality of crystal faces, which are specific to the crystal forming the three-dimensional substrate 12, and the inner surface, with excluding intersecting portions, at which the plurality of propagating surface zones 12a intersect with each other. With this configuration, as in the surface acoustic wave device 30 of the second embodiment described above with reference to FIG. 6, the surface acoustic device can be used as an environmental difference detecting apparatus, which is capable of detecting an environmental difference more precisely.

Furthermore, in the present embodiment, as in the surface acoustic wave device 30 of the second embodiment described above with reference to FIG. 6, it is preferable that, in the case where the three-dimensional substrate 12 is formed of the $Li_2B_4O_7$ crystal as described above, the transmitting and receiving portion of the electro-acoustic transducing element 14, which is capable to excite the surface acoustic wave along the inner surface of the three-dimensional substrate 12 and to propagate the surface acoustic wave along the inner surface and to receive the surface acoustic wave propagating along the inner surface, includes a part of the line of intersection (outermost circumferential line 12b) on the inner surface of the three-dimensional substrate 12. With such an arrangement of the transmitting and receiving portion of the electro-acoustic transducing element 14, it is possible to improve efficiency of the transmitting and receiving portion of the electro-acoustic transducing element 14 for exciting and receiving the surface acoustic wave.

In addition to such an arrangement, in the case where the three-dimensional substrate 12 is formed of the $Li_2B_4O_7$ crystal as described above and the outermost circumferential line 12b is specified as shown in FIG. 2, it is more preferable that the transmitting and receiving portion of the electro-acoustic transducing element 14 is arranged in the band shaped area AA indicating between 75° and 105° in the arbitrary direction from the above described C axis in order to improve the above-described efficiency of the transmitting and receiving portion of the electro-acoustic transducing element 14 more remarkably.

Fourth Embodiment

Figure 8:
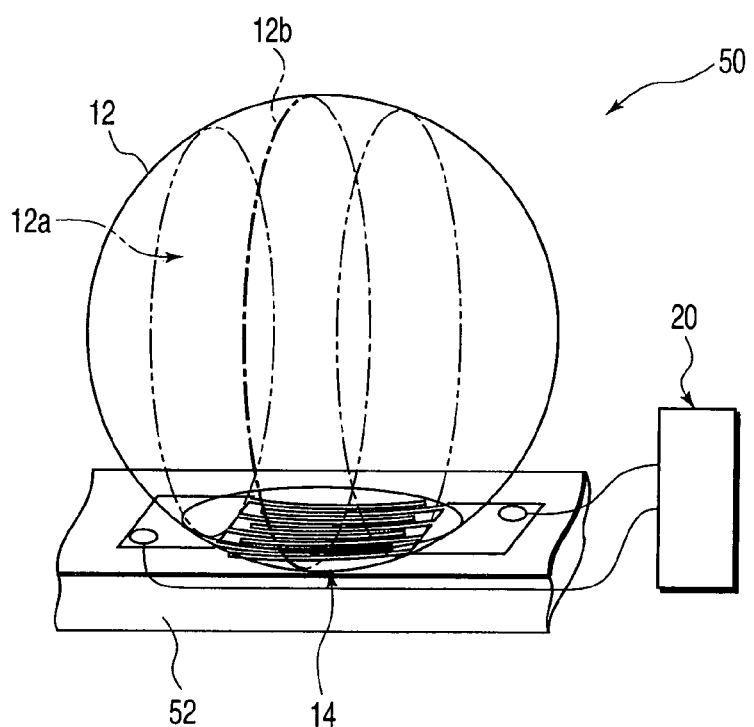
FIG. 8 is a perspective view schematically showing a surface acoustic wave device according to a fourth embodiment of the present invention.
Figure 9:
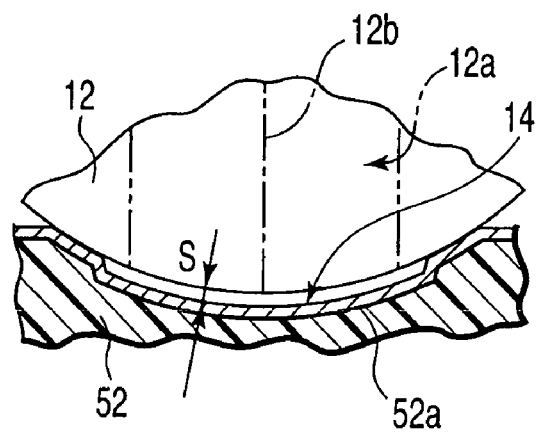
FIG. 9 is a partial cross sectional view schematically showing that an electro-acoustic transducing element is formed on a base for the three-dimensional substrate of the surface acoustic wave device shown in FIG. 8 so as to be arranged to face a band shaped propagating surface zone along the outer surface of the three-dimensional substrate with a predetermined gap therebetween.

Now, a fourth embodiment of the surface acoustic wave device according to the present invention will be described in detail with reference to FIGS. 8 and 9.

A surface acoustic wave device 50 according to the fourth embodiment comprises the spherically shaped three-dimensional substrate 12, the whole of which is formed of the $Li_2B_4O_7$ crystal or $Bi_{12}SiO_{20}$ crystal, as in the three-dimensional substrate 12 according to the above-described first embodiment and its modification. Along the outer surface of the three-dimensional substrate 12, a propagating surface zone 12a is specified so that the propagating surface zone 12a is continuous in an annular shape along the outermost circumferential line 12b, which is at least one of the plurality of lines of intersection between the plurality of crystal faces of the material for the three-dimensional substrate 12 and the outer surface thereof. The propagating surface zone 12a along the outer surface of the three-dimensional substrate 12 of the surface acoustic wave device 50 according to the present embodiment also preferably includes the outermost circumferential line 12b in the range of the propagating surface zone 12a, as in the propagating surface zone 12a along the outer surface of the three-dimensional substrate 12 according to the above-described first embodiment and its modification.

The surface acoustic wave device 50 of this embodiment is different from the surface acoustic wave device 10 according to the first embodiment or its modification in that the electro-acoustic transducing element 14, which is capable of exciting the surface acoustic wave along the propagating surface zone 12a along the outer surface of the three-dimensional substrate 12 and propagating the excited surface acoustic wave along the outermost circumferential line 12b in the range of the propagating surface zone 12a, is not directly formed on the outer surface of the three-dimensional substrate 12 within the propagating surface zone 12a.

In this embodiment, a base 52 for supporting a portion of the outer surface of the three-dimensional substrate 12 other than the propagating surface zone 12a has a propagating surface zone facing region 52a facing the propagating surface zone 12a with a predetermined gap S therebetween, and the electro-acoustic transducing element 14 is formed on the propagating surface zone facing region 52a of the base 52. The dimensions of the electro-acoustic transducing element 14 and the arrangement thereof with respect to the propagating surface zone 12a are identical to those in the case where the electro-acoustic transducing element 14 is directly formed on the outer surface of the three-dimensional substrate 12 within the propagating surface zone 12a in the surface acoustic wave device 10 according to the first embodiment or its modification.

In a case where the electro-acoustic transducing element 14 is the ladder shaped electrode 22 such as a comb shaped electrode, it is preferable that the predetermined gap S is equal to or smaller than ¼ of the arrangement pitch P (refer to FIG. 5) of the plurality of line elements (terminals) in the pattern of the ladder shaped electrode 22. When the predetermined gap S is greater than ¼ of the arrangement pitch P (refer to FIG. 5), it becomes difficult for the electro-acoustic transducing element 14 to always reliably excite a desired surface acoustic wave along the propagating surface zone 12a along the outer surface of the three-dimensional substrate 12.

The surface acoustic wave device 50 according to the fourth embodiment can be used in the same manner as that in the three-dimensional substrate 12 according to the above-described first embodiment and its modification. Where the electro-acoustic transducing element 14 is directly formed on the outer surface of the three-dimensional substrate 12 within the propagating surface zone 12a, the directly formed electro-acoustic transducing element 14 within the propagating surface zone 12a may very slightly affect the surface acoustic wave, which is excited and propagated along the propagating surface zone 12a. But, in the case where the electro-acoustic transducing element 14 faces the propagating surface zone 12a along the outer surface of the three-dimensional substrate 12 with the predetermined gap S therebetween, the above described adverse effect, which may be caused by the electro-acoustic transducing element 14 directly formed on the outer surface of the three-dimensional substrate 12 within the propagating surface zone 12a, can be eliminated. Consequently, in this embodiment, a change in the surface acoustic wave propagating along the propagating surface zone 12a can be sensed more precisely.

Further, in this embodiment, as in the surface acoustic wave device 30 of the second embodiment described above with reference to FIG. 6, propagating surface zone facing regions 52a of a plurality of bases 52 can be faced to a plurality of propagating surface zones 12a along a plurality of outermost circumferential lines 12b aligned with a plurality of lines of intersection between a plurality of crystal faces, which are specific to the crystal forming the three-dimensional substrate 12, and the outer surface thereof, excluding intersecting portions, at which the propagating surface zone 12a intersect with each other. And also, in this case, as in the surface acoustic wave device 30 of the second embodiment described above with reference to FIG. 6, the surface acoustic device can be used as an environmental difference detecting apparatus capable of more precisely detecting an environmental difference.

Furthermore, in this embodiment, as in the surface acoustic wave device 30 of the second embodiment described above with reference to FIG. 6, where the three-dimensional substrate 12 is formed of the $Li_2B_4O_7$ crystal as described above, it is preferable that the transmitting and receiving portion of the electro-acoustic transducing element 14, which is capable of exciting the surface acoustic wave along the outer surface of the three-dimensional substrate 12 and propagating the surface acoustic wave along the outer surface and receiving the surface acoustic wave propagating along the outer surface, is arranged so as to include a part of the line of intersection (outermost circumferential line 12b) along the outer surface of the three-dimensional substrate 12. With such an arrangement, it is possible to improve the efficiency of the transmitting and receiving portion of the electro-acoustic transducing element 14 for exciting and receiving the surface acoustic wave.

In addition to such an arrangement, in the case where the three-dimensional substrate 12 is formed of the $Li_2B_4O_7$ crystal as described above and the outermost circumferential line 12b is specified as shown in FIG. 2, it is more preferable that the transmitting and receiving portion of the electro-acoustic transducing element 14 is arranged along the outer surface of the three-dimensional substrate 12 in the band shaped area AA indicating between 75° and 105° in the arbitrary direction from the above described C axis as shown in FIG. 2, in order to improve the above described efficiency of the transmitting and receiving portion of the electro-acoustic transducing element 14 more remarkably.

Fifth Embodiment

Figure 10:
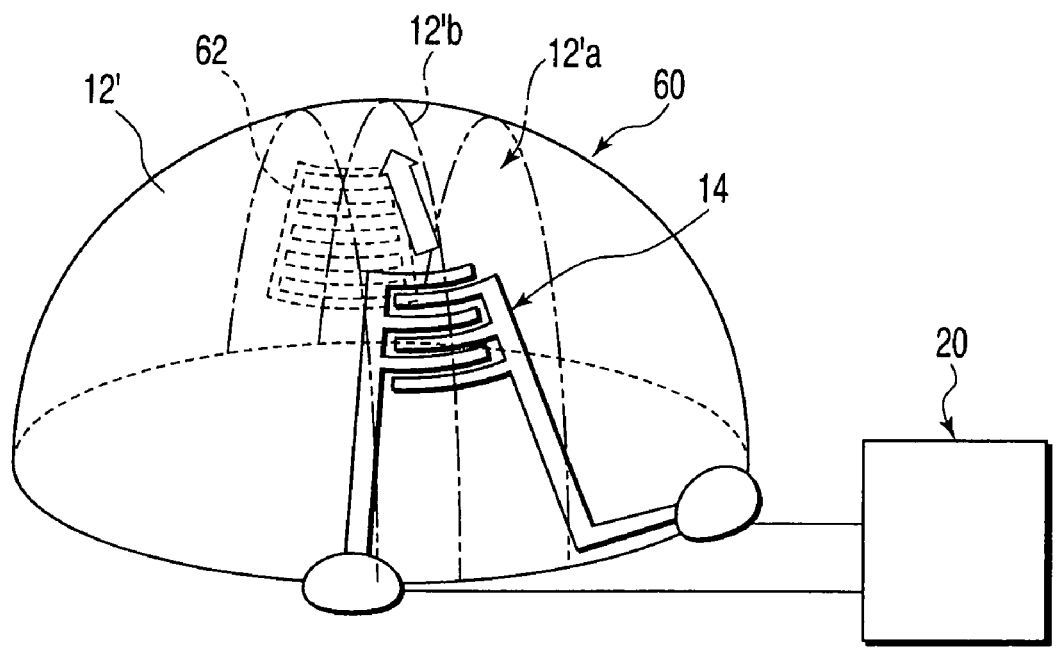
FIG. 10 is a perspective view schematically showing a surface acoustic wave device according to a fifth embodiment of the present invention.

Now, a fifth embodiment of the surface acoustic wave device according to the present invention will be described in detail with reference to FIG. 10.

A surface acoustic wave device 60 according to the fifth embodiment comprises a three-dimensional substrate 12' having a semispherical shape, and an outer surface of the three-dimensional substrate 12' includes a band shaped propagating surface zone 12'a made of at least a part of an annular continuous curved surface along which a surface acoustic wave can propagate.

The whole of the semi-spherically shaped three-dimensional substrate 12' is formed of a $Li_2B_4O_7$ crystal or $Bi_{12}SiO_{20}$ crystal, as in the three-dimensional substrate 12 according to the above-described first embodiment and its modification. And, at least one outermost circumferential line 12'b, which serves as a reference for extending the propagation surface zone 12'a continuously, is specified on the semi-spherically shaped outer surface of the three-dimensional substrate 12' of the surface acoustic wave device 60 according to the fifth embodiment to be aligned with a line of intersection between at least one of the plurality of specific crystal faces of the crystal forming the three-dimensional substrate 12' and the semi-spherically shaped outer surface thereof, in the same manner as in the case where the outermost circumferential line 12b, which serves as a reference for extending the propagation surface zone 12a continuously, is specified on the spherically shaped outer surface of the three-dimensional substrate 12 of the surface acoustic wave device according to the first embodiment or its modification to be aligned with a line of intersection between at least one of the plurality of specific crystal faces of the crystal forming the three-dimensional substrate 12 and the spherically shaped outer surface thereof. And, the outermost circumferential line 12'b is preferably included in the range of the propagating surface zone 12'a.

A method for specifying the outermost circumferential line 12'b serving as a reference for extending the propagating surface zone 12'a along the outer surface of the three-dimensional substrate 12' of the present embodiment is identical to that for specifying the outermost circumferential line 12b on the outer surface of the three-dimensional substrate 12 according to the above-described first embodiment and its modification.

In this embodiment, the electro-acoustic transducing element 14 is directly formed on the outer surface of the three-dimensional substrate 12' of the present embodiment within the propagating surface zone 12'a so as to propagate the surface acoustic wave along the outermost circumferential line 12'b in the range of the propagating surface zone 12'a while keeping its energy of at least 80% or more, and the above described electro-acoustic transducing element control unit 20 is connected to the electro-acoustic transducing element 14.

In this embodiment, a surface acoustic wave reflector 62 is formed at a position distant from the electro-acoustic transducing element 14 in a propagating direction of the surface acoustic wave, which is excited in the range of the propagating surface zone 12'a by the electro-acoustic transducing element 14 and which propagates along the outermost circumferential line 12'b in the range of the propagating surface zone 12'a. The surface acoustic reflector 62 reflects the surface acoustic wave, which propagates along the propagating surface zone 12'a from the electro-acoustic transducing element 14 toward the surface acoustic wave reflector 62, to be oriented toward the electro-acoustic transducing element 14 via the same passage.

Also in this embodiment, a portion of the outer surface other than the propagating surface zone 12'a may be formed in an arbitrary shape as long as the propagating surface zone 12'a is specified in accordance with the predetermined method described above.

In this embodiment, a portion of the three-dimensional substrate 12' other than the propagating surface zone 12'a is supported on a base (not shown).

In this embodiment, the acoustic surface wave, which is excited along the propagating surface zone 12'a made of a part of the annular shaped curved surface by the electro-acoustic transducing element 14 and which propagates along the propagating surface zone 12'a without attenuating significantly, changes in response to a variety of changes in a fluid (gas or liquid) including in an outer space that is an environment, with which the propagating surface zone 12'a along the outer surface of the three-dimensional substrate 12' comes into contact. And, the surface acoustic wave device 60 of the present embodiment can detect a change in the environment, i.e., a difference in the environment, by receiving the change in the signal, which is generated from the electro-acoustic transducing element 14, in the electro-acoustic transducing element control unit 20.

Further, in this embodiment, as in the surface acoustic wave device 30 of the second embodiment described above with reference to FIG. 6, a plurality of electro-acoustic transducing elements 14, each of which connected to the electro-acoustic transducing element control unit 20, can be formed along a plurality of propagating surface zones 12'a along a plurality of outermost circumferential lines 12'b aligned with a plurality of lines of intersection between a plurality of crystal faces, which are specific to the crystal forming the three-dimensional substrate 12', and the outer surface thereof, with excluding intersecting portions, at which the plurality of propagating surface zones 12'a intersect with each other. In this case, the surface acoustic wave reflector 62 is mounted at a position opposed to the surface acoustic transducing element 14 in each of the plurality of propagating surface zones 12'a excluding an intersection portion, with which other propagating surface zone 12'a intersects.

Furthermore, in the present embodiment, as in the surface acoustic wave device 30 of the second embodiment described above with reference to FIG. 6, it is preferable that, in the case where the three-dimensional substrate 12' is formed of the $Li_2B_4O_7$ crystal as described above, the transmitting and receiving portion of the electro-acoustic transducing element 14, which is capable to excite the surface acoustic wave along the inner surface of the three-dimensional substrate 12' and to propagate the surface acoustic wave along the inner surface and to receive the surface acoustic wave propagating along the outer surface, includes a part of the line of intersection (outermost circumferential line 12'b) on the inner surface of the three-dimensional substrate 12'. With such an arrangement of the transmitting and receiving portion of the electro-acoustic transducing element 14, it is possible to improve efficiency of the transmitting and receiving portion of the electro-acoustic transducing element 14 for exciting and receiving the surface acoustic wave.

In addition to such an arrangement, in the case where the three-dimensional substrate 12 is formed of the $Li_2B_4O_7$ crystal as described above and the outermost circumferential line 12'b is specified as shown in FIG. 2, it is more preferable that the transmitting and receiving portion of the electro-acoustic transducing element 14 is arranged in the band shaped area AA indicating between 75° and 105° in the arbitrary direction from the above described C axis in order to improve the above-described efficiency of the transmitting and receiving portion of the electro-acoustic transducing element 14 more remarkably.

Furthermore, as in the surface acoustic wave device 40 of the third embodiment described above with reference to FIG. 7, this embodiment can be modified such that the propagating surface zone 12'a made of at least a part of the annular curved surface and including the outermost circumferential line 12' is specified on, for example, a semi-spherically shaped recessed portion or an inner surface of a semi-spherically shaped cavity formed on or in the three-dimensional substrate 12', and that the electro-acoustic transducing element 14 and the surface acoustic wave reflector 62 are mounted along the propagating surface zone 12'a so as to be spaced from each other and opposed to each other along the outermost circumferential line 12'a.

Still furthermore, in the present embodiment, as in the surface acoustic wave device 50 of the fourth embodiment described above with reference to FIGS. 8 and 9, the electro-acoustic transducing element 14 can be formed on the above-descried base (not shown) so as to face the propagating surface zone 12'a with the predetermined gap S therebetween, instead of directly forming the electro-acoustic transducing element 14 on the outer surface of the three-dimensional substrate 12' within the propagating surface zone 12'a.

Yet furthermore, another electro-acoustic transducing element 14 connected to the electro-acoustic transducing element control unit 20 described previously can be used instead of the surface acoustic wave reflector 62.

Sixth Embodiment

Hereinafter, a sixth embodiment of the surface acoustic wave device according to the present invention will be described in detail with reference to FIGS. 11 to 17 included in the accompanying drawings.

Figure 11:
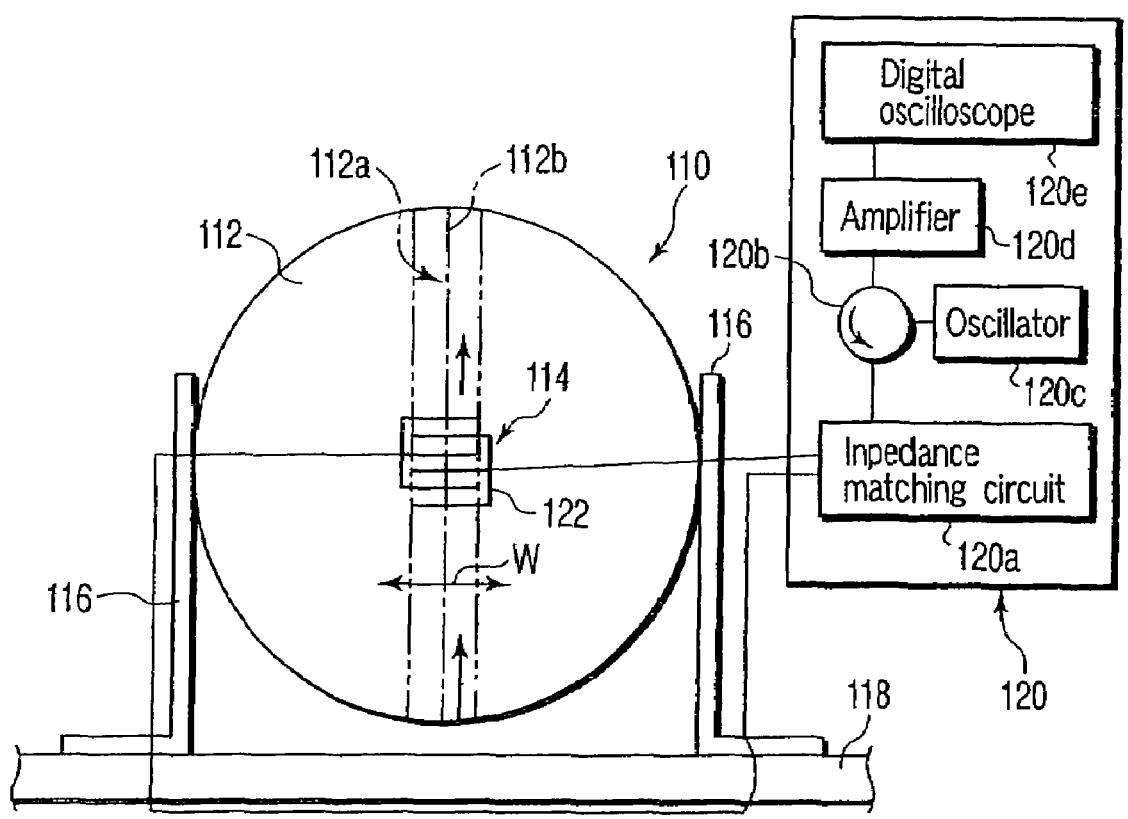
FIG. 11 is a schematic view of a surface acoustic wave device according to a sixth embodiment of the present invention.

FIG. 11 shows an appearance of a surface acoustic wave device 110 according to the sixth embodiment. The surface acoustic wave device 110 comprises: a three-dimensional substrate 112 having a surface, which includes a band shaped propagating surface zone 112a made of at least a part of a continuous annular curved surface and which is capable to propagate a surface acoustic wave; and an electro-acoustic transducing element 114, which is capable of exciting the surface acoustic wave along the propagating surface zone 112a and propagating the surface acoustic wave along the propagating surface zone 112a and receiving the surface acoustic wave propagating along the propagating surface zone 112a.

Here, the band shaped propagating surface zone 112a is drawn such that a dimension in its widthwise direction W is uniform at any points in a direction in which the band shaped propagating surface zone 112a is continuous in the annular shape, in order to simplify the drawing of FIG. 11. However, in actuality, while the surface acoustic wave propagates in the direction in which the band shaped propagating surface zone 112a is continuous in the annular shape along the surface of the three-dimensional substrate 112, the dimension of the surface acoustic wave in the widthwise direction W may be uniform as shown in FIG. 11 or may repeatedly diverge and converge.

In any case, it is practically desired that the surface acoustic wave propagates along the band shaped propagating surface zone 112a for a desired distance from the electro-acoustic transducing element 114 or per one circulation, while keeping at least 80% or more of energy thereof.

In this embodiment, whole of the three-dimensional substrate 112 is formed of a $LiNbO_3$ crystal of a trigonal system in a spherical shape. Therefore, in this embodiment, the band shaped propagating surface zone 112a is continuous in the annular shape along the spherically shaped surface of the three-dimensional substrate 112. The band shaped propagating surface zone 112a is continuous along an outermost circumferential line 112b of the three-dimensional substrate 112, and preferably, the outermost circumferential line 112b is included in the range of the band shaped propagating surface zone 112a.

On the outer surface of the three-dimensional substrate 112, the outermost circumferential line 112b, as shown in FIG. 12, coincides with a line of intersection between one crystal face of the $LiNbO_3$ crystal and the outer surface of the three-dimensional substrate 112, a normal line of the crystal face being a crystal axis CA specified by rotating a +Y axis that is one crystal axis of the $LiNbO_3$ crystal by 20° in a +Z direction with an X axis being a rotational center. That is, the outermost circumferential line 112b along which the band shaped propagating surface zone 112a extends along one crystal face of the $LiNbO_3$ crystal on the outer surface of the three-dimensional substrate 112. While the surface acoustic wave propagates along the above described crystal face on the outer surface of the three-dimensional substrate 112, a large energy diffusion of the surface acoustic wave will not occur in a direction, which crosses the above crystal face. Thus, the surface acoustic wave can propagate most efficiently along the outer surface of the three-dimensional substrate 112.

The LiNbO$_3$ crystal forming the three-dimensional substrate 112 is the trigonal system, and thus, has three crystal axes +Y, which are separated from each other by 120° in one plane as shown in FIG. 13. Therefore, three outermost circumferential lines 112*b* can be specified on the spherically shaped outer surface of the three-dimensional substrate 112 formed of the LiNbO$_3$ crystal, by three lines of intersection between three crystal faces, each normal line of which is each of three crystal axes CA specified by rotating each of these three crystal axes +Y by 20° in the +Z direction with the X axis being a rotational center, and the outer surface of the three-dimensional substrate 112. And, three propagating surface zones 112*a*, which are continuous as described above along the three outermost circumferential lines 112*b*, can be specified on the spherically shaped outer surface of the three-dimensional substrate 112 formed of the LiNbO$_3$ crystal.

On the outer surface of the three-dimensional substrate 112 according to the sixth embodiment and formed of the LiNbO$_3$ crystal of the trigonal system in the spherical shape, it is also possible to specify the outermost circumferential line 112*b*, along which the propagating surface zone 112*a* is continuous, as follows.

That is, on the outer surface of the three-dimensional substrate 112, the outermost circumferential line 112*b* is, as shown in FIG. 14, aligned with a line of intersection between a crystal face of the three-dimensional substrate 112 formed of the LiNbO$_3$ crystal and the outer surface of the three-dimensional substrate 112, a normal line of the crystal face being a crystal axis CB specified by rotating the +Y axis that is one crystal axis of the LiNbO$_3$ crystal by 26° in a −Z direction with the X axis being a rotational center. In this case, this means that the outermost circumferential line 112*b*, along which the propagating surface zone 112*a* extends along the outer surface of the three-dimensional substrate 112, extends on one crystal face other than the above described three crystal faces, each normal line of which is the crystal axis CA specified by rotating each of the above described three +Y axes in the LiNbO$_3$ crystal by 20° in the +Z direction around the X axis. While a surface acoustic wave propagates along such another crystal face on the outer surface of the three-dimensional substrate 112, significant diffusion of energy of the surface acoustic wave does not occur in a direction intersecting with such another crystal face, thus making it possible to propagate the surface acoustic wave along the outer surface of the three-dimensional substrate 112 most efficiently, as in the above described case where the surface acoustic wave propagates along each of the above described three crystal faces.

Since the LiNbO$_3$ crystal forming the three-dimensional substrate 112 is the trigonal system and has the three crystal axes +Y, which are separated from each other by 120° in one plane as shown in FIG. 15, other three outermost circumferential lines 112*b* can be specified on the spherically shaped outer surface of the three-dimensional substrate 112 formed of the LiNbO$_3$ crystal, by three lines of intersection between three crystal faces, each normal line of which is each of three crystal axes CB specified by rotating each of these three crystal axes +Y by 26° in the −Z direction with the X axis being a rotational center, and the outer surface of the three-dimensional substrate 112. And, other three propagating surface zones 112*a*, which are continuous as described above along the other three outermost circumferential lines 112*b*, can be specified on the spherically shaped outer surface of the three-dimensional substrate 112 formed of the LiNbO$_3$ crystal.

That is, since the LiNbO$_3$ crystal forming the three-dimensional substrate 112 has a total of six crystal faces, it is possible to specify a total of six outermost circumferential lines 112*b* on the outer surface of the three-dimensional substrate 112 wholly formed of the LiNbO$_3$ crystal.

In addition, it is possible to visually estimate an actual width of the surface acoustic wave, which propagates along the surface of the three-dimensional substrate 112, in a direction orthogonal to its propagating direction along the surface, because, for example, after depositing water droplets on the surface, the surface acoustic wave does not propagate along a portion of the surface on which water droplets are deposited.

In general, in a case where a surface acoustic wave having a high frequency is excited by using a ladder shaped electrode as an electro-acoustic transducing element, an effective width of the ladder shaped electrode (that is, a dimension of a portion of the ladder shaped electrode, at that portion the ladder shaped electrode excites a surface acoustic wave along the surface of the three-dimensional substrate and propagates the excited wave in a desired direction and receives the surface acoustic wave propagating along the surface, in a direction orthogonal to the desired direction along the surface) is reduced. However, it is found that a surface acoustic wave exciting and receiving efficiency of the effective width of the ladder shaped electrode is extremely lowered where the effective width is greater than 1.5 times of a radius of curvature of a band shaped propagating surface zone (designated by reference numeral 112*a* in FIG. 11) on the outer surface in a direction, which is the above desired direction, orthogonal to an outermost circumferential line (designated by reference numeral 112*b* in FIG. 11).

Portions of the outer surface of the three-dimensional substrate 112, which are other than the propagating surface zone 112*a* along which the surface acoustic wave excited by the electro-acoustic transducing element 114 propagates, are supported on a base 118 by supporting arms 116. In order to have no effect on the surface acoustic wave propagating along the propagating surface zone 112*a*, nothing but the electro-acoustic transducing element 114 is brought into contact with the propagating surface zone 112*a*. Therefore, in the present embodiment, an electro-acoustic transducing element control unit 120, which makes the electro-acoustic transducing element 114 excite the surface acoustic wave along the propagating surface zone 112*a* and receives a signal from the electro-acoustic transducing element 114 when the electro-acoustic transducing element 114 receives the surface acoustic wave propagating along the propagating surface zone 112*a*, is connected to the electro-acoustic transducing element 114 by lead wires extending from the electro-acoustic transducing element 114 on the portions of the outer surface of the three-dimensional substrate 112 other than the propagating surface zone 112*a*. The electro-acoustic transducing element control unit 120 comprises, for example, an impedance matching circuit 120*a*, a circulator 120*b*, an oscillator 120*c* including a high frequency power supply, an amplifier 120*d*, and a digital oscilloscope 120*e*, etc. as shown in FIG. 11. A high frequency radio wave receiving antenna can also be used instead of the oscillator 120*c*.

As shown in FIG. 16, it is preferable that the electro-acoustic transducing element 114 is configured so that an orientation MD, in which a flow density of energy of a surface acoustic wave excited along the propagating surface zone 112a becomes maximum, is within 20° with respect to the outermost circumferential line 112b. This angle is more preferably within 10°, and further preferably within 5° This means that, as long as the surface acoustic wave excited along the propagating surface zone 112a by the electro-surface transducing element 114 can circulate at a small attenuation rate such that, for example, 80% or more of energy can be maintained every circulation along the outermost circumferential line 12b on the outer surface of the three-dimensional substrate 112, the surface acoustic wave may be diffused from the outermost circumferential line 112b more than a width of the surface acoustic wave immediately after it is excited, while the surface acoustic wave propagates, but it is preferable that the surface acoustic wave is excited by the electro-surface transducing element 114 such that the orientation MD is within the above described angles.

A phrase "along the outermost circumferential line" described with respect to the present invention means a case in which, when the surface acoustic wave circulates or propagates along a propagation passage, a direction, in which the flow density of energy of the surface acoustic wave becomes maximum, is preferably within 20°, more preferably within 10°, and further preferably within 5° with respect to the outermost circumferential line.

In this embodiment, the electro-acoustic transducing element 114 is directly formed on the outer surface of the three-dimensional substrate 112 within the propagating surface zone 112a. In this embodiment, the electro-acoustic transducing element 114 is a ladder shaped electrode 122 such as, for example, a comb shaped electrode, and can be directly formed on the outer surface with a variety of publicly known processes such as, for example, vapor deposition, printing, sputtering, and sol-gel techniques.

In the case where the electro-acoustic transducing element 114 is formed of the ladder shaped electrode 122, it is preferable that, as well shown in FIG. 17, the ladder shaped electrode 22 is configured so that a line extending along the outer surface of the three-dimensional substrate 112 and being orthogonal to a transmitting and receiving portion (a portion of the above described effective width) of the ladder shaped electrode 122 capable of exciting a surface acoustic wave along the propagating surface zone 112a and receiving the surface acoustic wave propagating along the propagating surface zone 112a, is included in a range equal to or smaller than 10° with respect to the outermost circumferential line 112b, along which the propagating surface zone 112a extends. In more detail, this means that it is preferable that an orthogonal line OL, which extends along the outer surface of the propagating surface zone 112a and which is orthogonal to the transmitting and receiving portion at each terminal (line element) 122a in the pattern of the ladder shaped electrode 122 [in the case of the ladder shaped electrode 122, the transmitting and receiving portion at each terminal (line element) 122a in the pattern of the ladder shaped electrode 122, overlapping each other in a direction along the outermost circumferential line 112b], is in a range equal to or smaller than 10° with respect to the outermost circumferential line 112b.

The reason is identical to the reason why it is preferable that the electro-acoustic transducing element 114 is configured so that the orientation MD, in which the flow density of energy of the surface acoustic wave excited along the propagating surface zone 112a becomes maximum, is within 20° with respect to the outermost circumferential line 112b, as described previously with reference to FIG. 16.

Further, it is preferable that an arrangement pitch P of the plurality of terminals 122a (see FIG. 17) in the pattern of the ladder shaped electrode 122 in a direction along the outermost circumferential line 112b is equal to or smaller than $\frac{1}{10}$ of the radius of curvature of the outermost circumferential line 112b. The arrangement pitch P is equivalent to one wavelength (i.e., vibration cycle) of the surface acoustic wave excited by the ladder shaped electrode 122.

When the wavelength of the surface acoustic wave (i.e., the arrangement pitch P of the plurality of terminals 122a in the pattern of the ladder shaped electrode 122) is greater than $\frac{1}{10}$ of the radius of curvature of the outermost circumferential line 112b included in the propagating surface zone 112a along which the surface acoustic wave propagates (in the case where the propagating surface zone 112a is a part of the spherical surface as in this embodiment, the radius of curvature is a radius of the spherical surface), a function of a geometrical feature of the curved propagating surface zone 112a to restrict diffusion of the surface acoustic wave propagating along the propagating surface zone 112a becomes weak. Therefore, in order to propagate a surface acoustic wave having a comparatively long wavelength along the propagating surface zone 112a on the surface of the three-dimensional substrate 112 for a desired distance, the radius of curvature of the outermost circumferential line 112b included in the propagation surface zone 112a must be preset so as to meet the above-described relationship with the above wavelength.

Consequently, it is preferable that the arrangement pitch is defined as described above to efficiently propagate a surface acoustic wave along the propagating surface zone 112b.

Inventors of the present invention actually form a spherically shaped three-dimensional substrate out of the LiNbO$_3$ crystal in accordance with this embodiment, and its diameter is 25.4 mm. And, a ladder shaped electrode to be used as an electro-acoustic transducing element is formed on the outer surface of the spherically shaped three-dimensional substrate at a position corresponding to the +X direction of the above crystal viewed from the center of the three-dimensional substrate. The ladder shaped electrode is formed by forming a film on the outer surface of the three-dimensional substrate with vapor deposition of 1000 angstroms of chrome or vapor deposition of 1000 angstroms of gold, and then by photolithography processing the film to make terminals (line elements) in a pattern of the ladder shaped electrode being orthogonal to a direction circulating on the above described spherically shaped outer surface around a direction obtained by rotating the +Y axis of the LiNbO$_3$ crystal by 20° in the +Z direction with the X axis being as a rotational center. An arrangement pitch P of the terminals (line elements) in the pattern of the ladder shaped electrode formed at this time is 0.532 mm. And, in the pattern, a width of each terminal (line element) is 0.133 mm and a plurality of terminals (line elements) are arranged at intervals of 0.133 mm, respectively. Further, when a desired pulse voltage is applied between the terminals (line elements) adjacent to each other, an electric field is generated between portions of the adjacent terminals (line elements) overlapping with each other. And, a length of the overlapping portion of each of the adjacent terminals (line elements) is 3.1 mm.

Although the dimensions of the ladder shaped electrode, which is formed on the outer surface of the spherically shaped three-dimensional substrate of the LiNbO$_3$ crystal by the inventors of the present application and which is used actually as an electro-acoustic transducing element, are described, a ladder shaped electrode made of any conventionally known material and/or having any dimensions and/or any shape can be used as long as it can achieve required functions or technical advantages of the present invention on the outer surface of the three-dimensional substrate.

When an impulse signal of 2 nanoseconds in half-value width is applied at a voltage of 100V to the ladder shaped electrode of the spherically shaped surface acoustic wave device configured as described above, it is verified by a digital oscilloscope that a burst signal having a center frequency of about 6.5 MHz is repeatedly outputted from the above-described ladder shaped electrode at least 50 times at intervals of 21.8 μs in the above described circulating direction. This means that a surface acoustic wave circulates along the outer surface of the spherically shaped three-dimensional substrate of the $LiNbO_3$ crystal having a diameter of 25.4 mm as described above, at least 50 times or more at an average speed of 3658 m/s in the direction in which the surface acoustic wave circulates.

The inventors of the present invention form a ladder shaped electrode, which is used as an electro-acoustic transducing element, in a different way as that described above at the same position as that described above on the outer surface of the spherically shaped three-dimensional substrate made of the $LiNbO_3$ crystal having the diameter equal to that described above. That is, in this case, the ladder shaped electrode is formed by forming a film on the outer surface of the three-dimensional substrate with vapor deposition of 1000 angstroms of chrome or vapor deposition of 1000 angstroms of gold, and then by photolithography processing the film to make terminals (line elements) in a pattern of the ladder shaped electrode being orthogonal to a direction circulating on the above described spherically shaped outer surface around a direction obtained by rotating the +Y axis of the $LiNbO_3$ crystal by 26° in the −Z direction with the X axis being as a rotational center.

When an impulse signal is applied in the same manner as described above to the ladder shaped electrode of the spherically shaped surface acoustic wave device configured as described above, it is verified by the digital oscilloscope that a burst signal having a center frequency of about 6.5 MHz is repeatedly outputted from the above-described ladder shaped electrode at least 50 times at intervals of 22.5 μs in the above described circulating direction. This means that a surface acoustic wave circulates along the outer surface of the spherically shaped three-dimensional substrate of the $LiNbO_3$ crystal having the diameter of 25.4 mm as described above, at least 50 times or more at an average speed of 3540 m/s in the direction in which the surface acoustic wave circulates.

Then, a water-containing cotton swab is brought into contact with a position on the outer surface of each of two types of the spherically shaped surface acoustic wave devices configured as described above by the inventors of the present application, the position being distant from the ladder shaped electrode in the above described circulating direction (i.e., on the circulating passage of the surface acoustic wave). As a result, it has been found that, when an impulse signal is applied to the ladder shaped electrode as described above, no output can be generated from the ladder shaped electrode and the circulation of the surface acoustic wave is inhibited. Further, the water-containing cotton swab is brought into contact with a position on the outer surface of each of two types of the spherically shaped surface acoustic wave devices configured as described above, the position being distant from the ladder shaped electrode for 5 mm or more in a direction orthogonal to the above circulating direction (i.e., a position detached from the circulating passage of the surface acoustic wave). As a result, it has been found that, when an impulse signal is applied to the ladder shaped electrode as described above, a burst signal is repeatedly outputted as described above from the ladder shaped electrode, and the above described circulation of the surface acoustic wave is not inhibited.

First Modification of Sixth Embodiment

Figure 18:
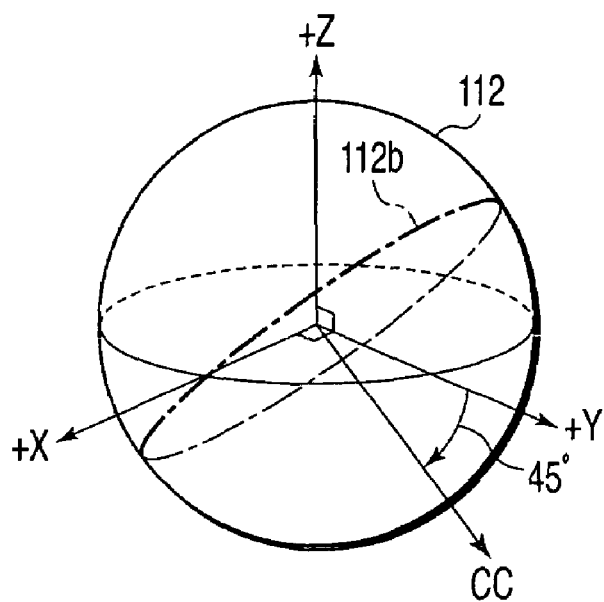
FIG. 18 is a perspective view schematically showing, in a case where a whole three-dimensional substrate of the surface acoustic wave device according to a first modification of the sixth embodiment of the invention is formed of a $LiTaO_3$ crystal, how to define an outermost circumferential line serving as a reference of a band shaped zone for propagating a surface acoustic wave along an outer surface of the three-dimensional substrate, along one of three crystal faces of the $LiTaO_3$ crystal.
Figure 19:
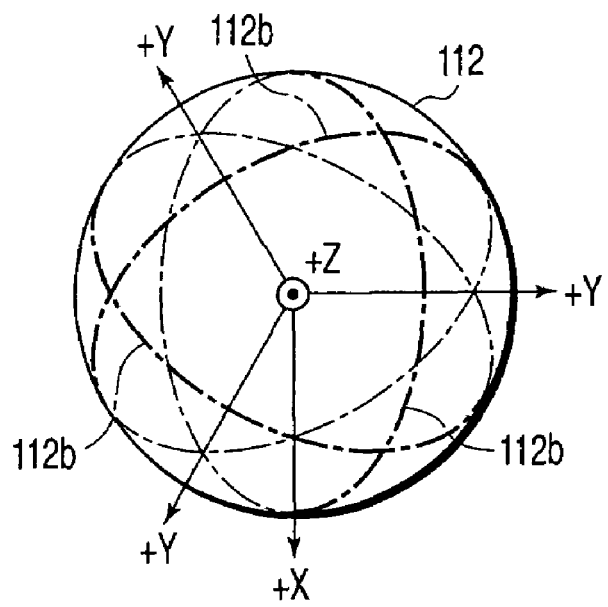
FIG. 19 is a schematic view in which the three-dimensional substrate of FIG. 18 is seen from a +Z direction side toward a −Z direction side in order to show three outermost circumferential lines serving as references for three band shaped propagating surface zones set along the outer surface of the three-dimensional substrate as shown in FIG. 18.

Now, with reference to FIGS. 18 and 19, a first modification of the sixth embodiment of the surface acoustic wave device according to the present invention will de described in detail.

In a surface acoustic wave device of this modification, the three-dimensional substrate 112, which is formed of the $LiNbO_3$ Crystal of the trigonal system in the sixth embodiment, is formed of a $LiTaO_3$ crystal of the similar trigonal system in the spherical shape. Concurrently, a method for specifying the outermost circumferential line 112b on the outer surface of the three-dimensional substrate 112 is also different from that in the case of the three-dimensional substrate 112 formed of the $LiNbO_3$ of the trigonal system in the sixth embodiment. However, structural elements other than those described above are identical to those of the surface acoustic device of the sixth embodiment described previously.

In the surface acoustic wave device of this first modification, the outermost circumferential line 112b is aligned with a line of intersection between one crystal face of the three-dimensional substrate 112, which is wholly formed of the $LiNbO_3$ crystal of the trigonal system, and the outer surface of the three-dimensional substrate 112 on the outer surface, a normal line of the crystal face being a crystal axis CC specified by rotating a +Y axis that is one crystal axis of the $LiTaO_3$ crystal by 45° in a −Z direction with an X axis being a rotational center, as shown in FIG. 18. And, while the surface acoustic wave propagates along such one crystal face along the outer surface of the three-dimensional substrate 112, significant diffusion of energy of the surface acoustic wave does not occur in a direction intersecting with the above-described crystal face, thus making it possible to propagate the surface acoustic wave along the outer surface of the three-dimensional substrate 112 most efficiently, as is the case of the crystal face of the sixth embodiment.

Since the $LiTaO_3$ crystal forming the three-dimensional substrate 112 is the trigonal system, it has three crystal axes +Y separating from each other for 120° in one plane, as shown in FIG. 19. Therefore, where three lines of intersection specified as described above with respect to the three crystal axes +Y are defined as three outermost circumferential lines 112b, it is possible to specify three propagating surface zones 112a, which are continuous as described above along the three outermost circumferential lines 112b.

Second Modification of Sixth Embodiment

Now, with reference to FIGS. 20 and 21, a second modification of the sixth embodiment of the surface acoustic wave device according to the present invention will be described in detail.

In a surface acoustic wave device of this modification, the three-dimensional substrate 112, which is formed of the $LiNbO_3$ crystal of the trigonal system in the sixth embodiment, is formed of a quartz crystal of the similar trigonal system in the spherical shape. Concurrently, a method for specifying the outermost circumferential line 112b on the outer surface of the three-dimensional substrate 112 is also different from that in the case of the three-dimensional substrate 112 formed of the LiNbO$_3$ of the trigonal system in the sixth embodiment. However, structural elements other than those described above are identical to those of the surface acoustic device of the sixth embodiment described previously.

In the surface acoustic wave device of this second modification, the outermost circumferential line 112*b* is aligned with a line of intersection between one crystal face of the three-dimensional substrate 112, which is wholly formed of the quartz crystal of the trigonal system, and the outer surface of the three-dimensional substrate 112 on the outer surface, a normal line of the crystal face being a +Y axis that is one crystal axis CD of the quartz crystal, as shown in FIG. 20. And, while the surface acoustic wave propagates along such one crystal face along the outer surface of the three-dimensional substrate 112, significant diffusion of energy of the surface acoustic wave does not occur in a direction intersecting with the above-described crystal face, thus making it possible to propagate the surface acoustic wave along the outer surface of the three-dimensional substrate 112 most efficiently, as is the case of the crystal face of the sixth embodiment.

Since the quartz crystal forming the three-dimensional substrate 112 is the trigonal system, it has three crystal axes +Y separating from each other for 120° in one plane, as shown in FIG. 21. Therefore, where three lines of intersection specified as described above with respect to the three crystal axes +Y are defined as three outermost circumferential lines 112*b*, it is possible to specify three propagating surface zones 112*a*, which are continuous as described above along the three outermost circumferential lines 112*b*.

In the surface acoustic wave devices 110 according to the above described sixth embodiment, and to its first and second modifications, a variety of dimensions of the three-dimensional substrate 112 and a variety of dimensions of the electro-acoustic transducing element 114 are set as follows. That is, the surface acoustic wave excited by the electro-acoustic transducing element 114 along the outer surface of the three-dimensional substrate 112 of the surface acoustic wave device 110 circulates along the outer surface in a direction, in which the propagating surface zone 112*a* is continuous in an annular shape along the outermost circumferential line 112*b* specified as described above, within the range of the propagating surface zone 112*a* at an energy exhaust rate that is substantially equal to or smaller than 20% per one circulation (i.e., while keeping 80% or more of energy per one circulation).

This means that the three-dimensional substrate 112 of the surface acoustic wave device 110 may be formed in any arbitrary shape other than the propagating surface zone 112*a*. For example, the three-dimensional substrate 112 can be formed in a ring-like doughnut shape, a barrel shape, a rugby ball shape, or a disk shape, each having the annular propagating surface zone 112*a* on its outer surface.

In the surface acoustic wave devices 110 according to the above-described sixth embodiment, and to its first and second modifications, when any change occurs in a fluid (gas or liquid) filled in a space, with which the propagating surface zone 112*a* comes into contact (i.e., when any change occurs in an external environment, with which the propagating surface zone 112*a* comes into contact), a change occurs in a propagation speed of the surface acoustic wave propagating along the propagating surface zone 112*a* or in a propagation time of the surface acoustic wave required for one circulation. That is, the surface acoustic wave device 110 can be used as an environmental difference detecting apparatus for detecting a change or a difference in an external environment.

Seventh Embodiment

Now, a seventh embodiment of the surface acoustic wave device according to the present invention will be described in detail with reference to FIG. 22.

In the present embodiment, the electro-acoustic transducing element 114 is formed as described above along each of an arbitrary plurality of propagating surface zones 122*a* (six zones in the sixth embodiment and three zones in each of its first and second modifications), that can be specified as described above on the outer surface of the three-dimensional substrate 112 of the surface acoustic wave device 110 according to any of the sixth embodiment and its first and second modifications, at a portion not intersecting with the other propagating surface zone 122*a*. And, each of the electro-acoustic transducing elements 114 is connected to the electro-acoustic transducing element control unit 120 described above.

Further, in the present embodiment, a support member 132 for supporting the three-dimensional substrate 112 on any base (not shown) is fixed at a position on the outer surface of the three-dimensional substrate 112 excluding the plurality of propagating surface zones 112*a*, along which the electro-acoustic transducing elements 114 are formed.

A surface acoustic wave device 130 according to the seventh embodiment and configured as described above is superior to the surface acoustic wave device 100 according to any of the sixth embodiment and its first and second modifications, when they are used as environmental difference detecting apparatuses.

The reason is as follows.

In the case where, as in the above-described surface acoustic wave device 110, only one electro-acoustic transducing element 114 and one electro-acoustic transducing element control unit 120 connected hereto are used, a slight change occurs in a propagation speed of the surface acoustic wave propagating along the propagating surface zone 112*a* or in a propagation time of the surface acoustic wave required for one circulation, when any physical change occurs in the surface acoustic wave element 110 due to an effect of the change in the above described external environment (for example, an expansion or a contraction of the three-dimensional substrate 112 due to a temperature change in the external environment).

Consequently, in order to more precisely detect a change in a fluid (gas or liquid) filled in a space, with which the propagating surface zone 112*a* comes into contact as described previously, a physical change of the surface acoustic wave device 11 due to the effect of the change in the external environment described above must be considered.

Figure 22:
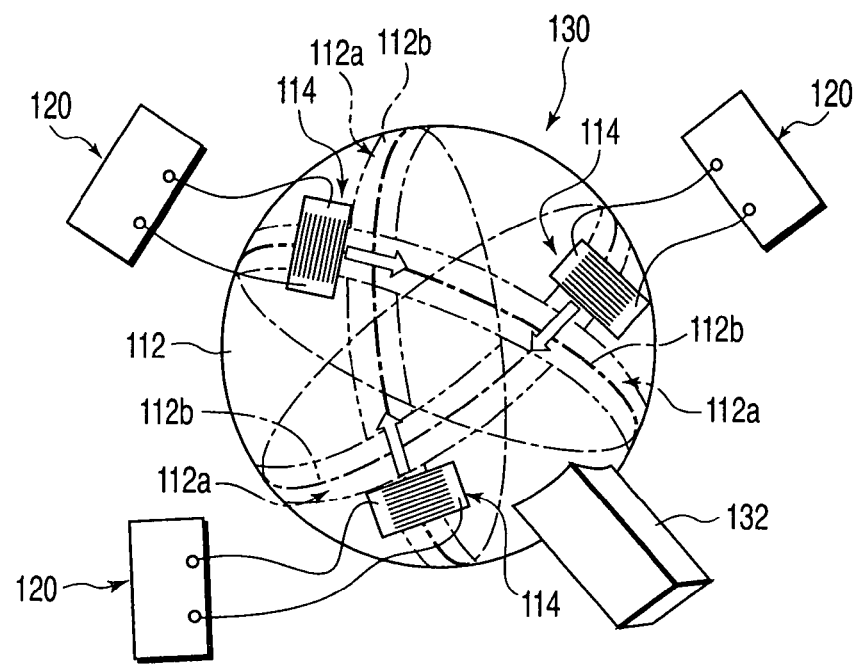
FIG. 22 is a perspective view schematically showing a surface acoustic wave device according to a seventh embodiment of the present invention.

The surface acoustic wave device 130 according to the seventh embodiment described with reference to FIG. 22 is configured so that at least one of the plurality of propagating surface zones 112*a*, along which the electro-acoustic transducing elements 114 are formed along the outer surface of the three-dimensional substrate 112, is isolated from an external environment, a change of which is to be detected, and that at least another of the plurality of propagating surface zones 112*a*, along which the electro-acoustic transducing elements 114 are formed, is brought into contact with the external environment.

With such a configuration, a signal generated from the electro-acoustic transducing element 114 along the propagating surface zone 112a, which is isolated from the external environment, and received by the electro-acoustic transducing element control unit 120 corresponding to the above described electro-acoustic transducing element 114, indicates a physical change of the surface acoustic wave device 110 due to the change in the external environment. In addition, a signal generated from the electro-acoustic transducing element 114 along the propagating surface zone 112a, which is in contact with the external environment, and received by the electro-acoustic transducing element control unit 20 corresponding to the above described electro-acoustic transducing element 114, indicates a change in the external environment, together with the physical change of the surface acoustic wave device 110, due to the change in external environment.

Accordingly, by subtracting the signal, which is generated from the electro-acoustic transducing element 114 along the propagating surface zone 112a isolated from the external environment and which is received by the electro-acoustic transducing element control unit 120 corresponding to the electro-acoustic transducing element 114, from the signal, which is generated from the electro-acoustic transducing element 114 along the propagating surface zone 112a come into contact with the external environment and which is received by the electro-acoustic transducing element control unit 120 corresponding to the electro-acoustic transducing element 114, it possible to purely detect only the change in the external environment.

Modification of Seventh Embodiment

Figure 23:
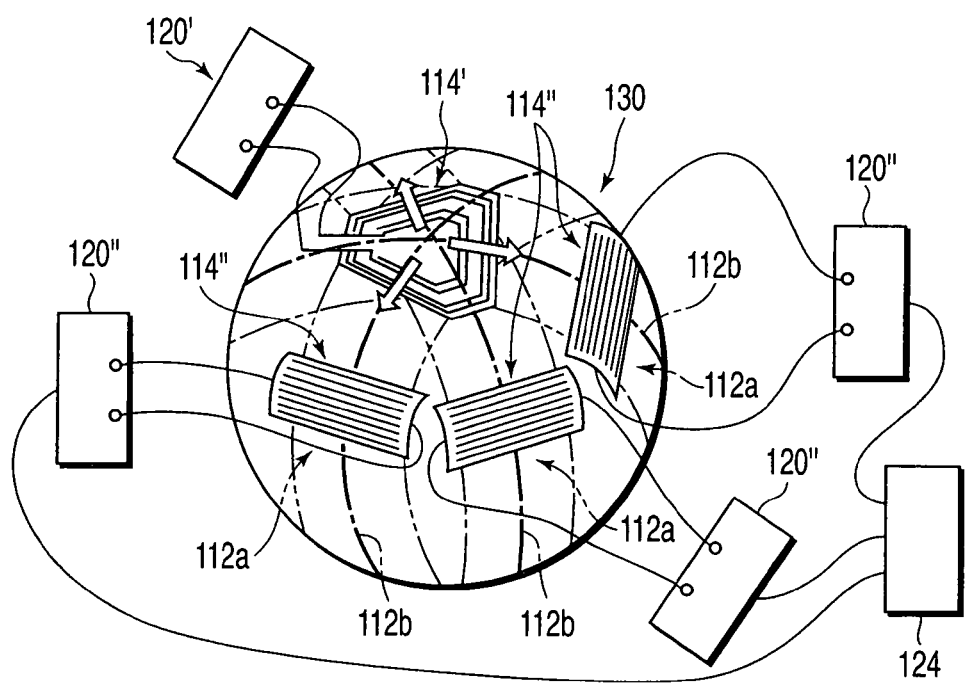
FIG. 23 is a perspective view schematically showing a surface acoustic wave device according to a modification of the seventh embodiment shown in FIG. 22.

FIG. 23 shows a modification of the surface acoustic wave device according to the seventh embodiment described above with reference to FIG. 22.

In this modification, a common electro-acoustic transducing element 114' for exciting surface acoustic waves, which is common to a plurality of propagating surface zones 112a, is formed at an intersecting region of the propagating surface zones 112a on the outer surface of the three-dimensional substrate 112. The common electro-acoustic transducing element 114' is connected to a common electro-acoustic element control unit 120', and the common electro-acoustic element control unit 120' controls the common electro-acoustic transducing element 114' so as to excite and propagate surface acoustic waves having the same frequency each other along the plurality of propagating surface zones 112a at the same time.

Further, an electro-acoustic transducing element 114" for receiving a surface acoustic wave, is formed along each of the plurality of propagating surface zones 112a at a position, which does not overlap with the other propagating surface zone. Each of the plurality of electro-acoustic transducing elements 114" for receiving is connected to a receiving electro-acoustic transducing element control unit 120", and is further connected to a signal difference detecting means 24 via the respective receiving electro-acoustic transducing element control unit 120", the signal difference detecting means 24 detecting a difference between signals received by the respective electro-acoustic transducing element control units 120".

Normally, the plurality of receiving electro-acoustic transducing elements 114" receive surface acoustic waves from the plurality of propagating surface zones 112a at the same time. However, for example, when a foreign matter such as a liquid comes into contact with each of the propagating surface zones 112a due to a change in an environment in a part of an external space adjacent to the each of the propagating surface zones 112a, a difference occurs between a propagation speed of a surface acoustic wave along the each of the propagating surface zones 112a, with which such a foreign matter comes into contact, and a propagation speed of a surface acoustic wave in each of the remaining plural propagating surface zones 112a, with which no foreign matter comes into contact. Due to this difference, the signal difference detecting means 124 connected to the plurality of receiving electro-acoustic transducing elements 114" via the plurality of receiving electro-acoustic transducing element control units 120" can detect a degree of a change in the environment in the part of the above external space.

In this modification, one common excitation electro-acoustic transducing element 114' and the plurality of receiving electro-acoustic transducing elements 114" are formed with respect to the plurality of propagating surface zones 112a. Thus, the one common excitation electro-acoustic element control unit 120' is provided for the one common excitation electro-acoustic transducing element 114', and the plurality of receiving electro-acoustic transducing element control units 120" are provided for the plurality of receiving electro-acoustic transducing elements 114".

A circuit design for the common excitation electro-acoustic element control unit 120' and that for each of the plurality of receiving electro-acoustic transducing element control units 120" in this modification are much easier as compared with a circuit design for each of the plurality of electro-acoustic transducing element control units 120 provided for the plurality of transmitting and receiving electro-acoustic transducing elements 114 formed along the plurality of propagating surface zones 112a in the seventh embodiment shown in FIG. 22.

Eighth Embodiment

Figure 24:
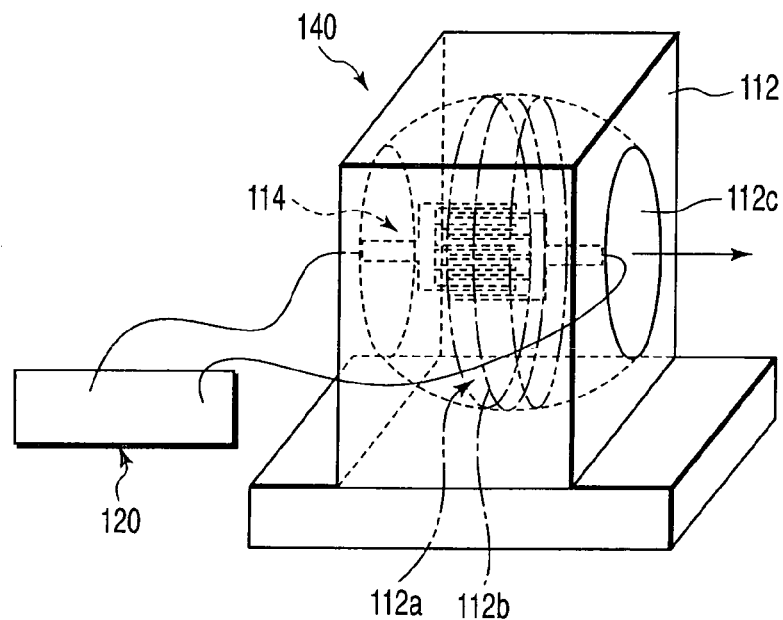
FIG. 24 is a perspective view schematically showing a surface acoustic wave device according to an eighth embodiment of the present invention.

Now, an eighth embodiment of the surface acoustic wave element according to the present invention will be described in detail with reference to FIG. 24.

A three-dimensional substrate 112 of a surface acoustic wave device 140 according to the eighth embodiment has a recessed or hollow portion, and the recessed portion or an inner surface 112c of the hollow portion includes a propagating surface zone 112a, which is a curved surface being continuous in an annular shape and along which a surface acoustic wave can propagate. FIG. 24 shows the three-dimensional substrate 112 having a through hole that is one kind of the hollow portion.

A whole of the three-dimensional substrate 112 is formed of a $LiNbO_3$ crystal, a $LiTaO_3$ crystal, or a quartz crystal, as the three-dimensional substrate 112 according to each of the sixth embodiment and its first or second modifications. And, at least one outermost circumferential line 112b is specified on the inner surface of the three-dimensional substrate 112 of the surface acoustic wave device 140 according to the eighth embodiment along a line of intersection between one of a plurality of crystal faces, which are particular to a kind of the crystal forming the three-dimensional substrate 112 of the surface acoustic wave device 140 according to the eighth embodiment, and the inner surface of the three-dimensional substrate 112, the outermost circumferential line 112b serving as a reference for extending the propagating surface zone 112a along the inner surface. Such a specifying manner of the at least one outermost circumferential line 112b on the inner surface of the three-dimensional substrate 112 is the same as that of the outermost circumferential line 112b on the outer surface of the three-dimensional substrate 112 according to each of the sixth embodiment and its first and second modifications, in which the outermost circumferential line 112b is specified along the line of intersection between one of the plurality of crystal faces, which are particular to the kind of the crystal forming the three-dimensional substrate 112 according to each of the sixth embodiment and its first and second modifications, and the outer surface of the three-dimensional substrate 112, the outermost circumferential line 112b serving as a reference for extending the propagating surface zone 112a along the outer surface. Consequently, the propagating surface zone 112a is specified along the inner surface so as to extend continuously along the outermost circumferential line 112b. The specifying manner of the propagating surface zone 112a along the inner surface of the three-dimensional substrate 112 according to this embodiment is the same as that of the propagating surface zone 112a along the inner surface of the three-dimensional substrate 112 according to each of the above described sixth embodiment and its first and second modifications. Therefore, the outermost circumferential line 112b is preferably included in the range of the propagating surface zone 112a along the inner surface.

Also in the propagating surface zone 112a along the inner surface of the three-dimensional substrate 12 of this embodiment, the electro-acoustic transducing element 114 is formed so as to propagate the surface acoustic wave along the outermost circumferential line 112b in the range of the propagating surface zone 112a without significantly attenuating it, and the above described electro-acoustic transducing element control unit 20 is connected to the electro-acoustic transducing element 114.

In this embodiment as well, a portion of the inner surface other than the propagating surface zone 112a may be formed in an arbitrary shape as long as the propagating surface zone 112a is specified in accordance with the above described predetermined manner.

In this embodiment, the acoustic surface wave, which is excited along the propagating surface zone 112a by the electro-acoustic transducing element 114 and which propagates along the propagating surface zone 112a while keeping its energy of, for example, 80% or more per one circulation without significant attenuation, changes in response to a variety of changes in a fluid (gas or liquid) passing through the internal space of a through hole that is an environment, with which the propagating surface zone 112a along the inner surface of the three-dimensional substrate 112 comes into contact. And, the surface acoustic wave device 140 of the present embodiment can detect a change in the environment, i.e., a difference in the environment, by receiving the change in the signal, which is generated from the electro-acoustic transducing element 114, in the electro-acoustic transducing element control unit 120.

Further, in this embodiment, as in the surface acoustic wave device 130 of the seventh embodiment described above with reference to FIG. 22, a plurality of electro-acoustic transducing elements 114, each of which is connected to an electro-acoustic transducing element control unit 120, can be formed along a plurality of propagating surface zones 112a along a plurality of outermost circumferential lines 12b aligned with a plurality of lines of intersection between a plurality of crystal faces, which are specific to the crystal forming the three-dimensional substrate 112, and the inner surface, with excluding intersecting portions, at which the plurality of propagating surface zones 112a intersect with each other. With this configuration, as in the surface acoustic wave device 130 of the seventh embodiment described above with reference to FIG. 22, the surface acoustic device can be used as an environmental difference detecting apparatus, which is capable of detecting an environmental difference more precisely.

More further, in this embodiment, as in the surface acoustic wave device 130 of the modification of the seventh embodiment described above with reference to FIG. 23, a common excitation electro-acoustic transducing element 114' can be formed along the outer surface of the three-dimensional substrate 112 at an intersection region of a plurality of propagating surface zones 112a along a plurality of outermost circumferential lines 12b aligned with a plurality of lines of intersection between a plurality of crystal faces, which are specific to the crystal forming the three-dimensional substrate 112, and the outer surface thereof, the common excitation electro-acoustic transducing elements 114' being used for the plurality of propagating surface zones 112a in common. And, at the same time, a plurality of receiving electro-acoustic transducing elements 114" can be formed along the plurality of propagating surface zones 112a excluding the intersection region. With this configuration, as in the surface acoustic wave device 130 of the modification of the seventh embodiment described above with reference to FIG. 23, the surface acoustic device can be used as an environmental difference detecting apparatus, which is capable of detecting an environmental difference more precisely.

Ninth Embodiment

Figure 25:
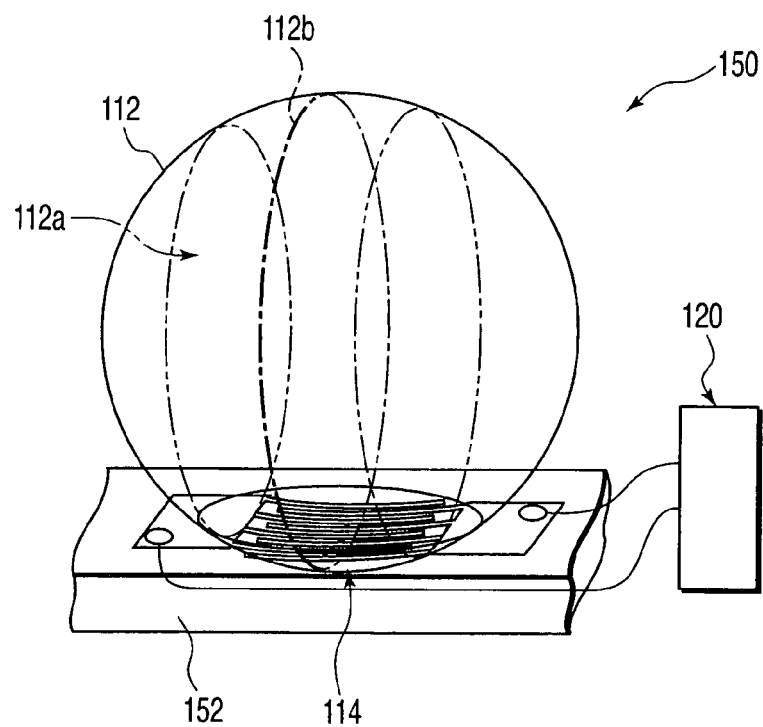
FIG. 25 is a perspective view schematically showing a surface acoustic wave device according to a ninth embodiment of the present invention.
Figure 26:
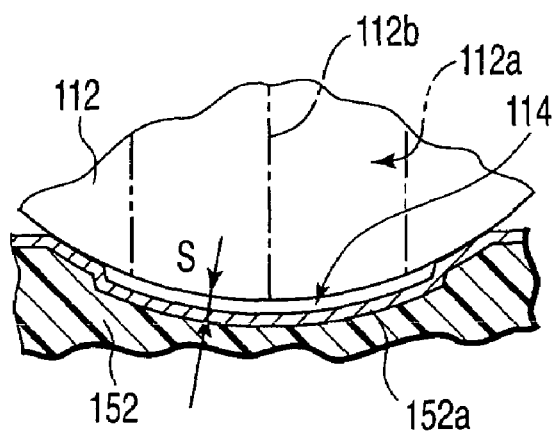
FIG. 26 is a partial cross sectional view schematically showing that an electro-acoustic transducing element is formed on a base for the three-dimensional substrate of the surface acoustic wave device shown in FIG. 25 so as to be arranged to face a band shaped propagating surface zone along the outer surface of the three-dimensional substrate with a predetermined gap therebetween.

Now, a ninth embodiment of the surface acoustic wave device according to the present invention will be described in detail with reference to FIGS. 25 and 26.

A surface acoustic wave device 150 according to the ninth embodiment comprises a spherically shaped three-dimensional substrate 112, a whole of which is formed of a $LiNbO_3$ crystal, a $LiTaO_3$ crystal, or a quartz crystal, as in the three-dimensional substrate 112 according to each of the above-described sixth embodiment and its first or second modifications. On an outer surface of the three-dimensional substrate 112, at least one of a plurality of lines of intersection between a plurality of crystal faces of the material of the three-dimensional substrate 112 and the outer surface thereof, is defined as the outermost circumferential line 112b, and the propagating surface zone 112a is specified along the outermost circumferential line 112b so as to be continuous in an annular shape. The propagating surface zone 112a along the outer surface of the three-dimensional substrate 112 of the surface acoustic wave device 150 according to this embodiment also preferably includes the outermost circumferential line 112b in the range of the propagating surface zone 112a, as in the propagating surface zone 112a along the outer surface of the three-dimensional substrate 112 according to each of the above-described sixth embodiment and its first or second modifications.

The surface acoustic wave device 150 of the present embodiment is different from the surface acoustic wave device 110 according to each of the sixth embodiment and its first and second modifications in that the electro-acoustic transducing element 114, which is capable of exciting a surface acoustic wave along the propagating surface zone 112a along the outer surface of the three-dimensional substrate 112 and propagating the excited surface acoustic wave along the outermost circumferential line 112b in the range of the propagating surface zone 112a, is not directly formed in the propagating surface zone 112a on the outer surface of the three-dimensional substrate 112.

In this embodiment, a base 152 for supporting a portion of the outer surface of the three-dimensional substrate 112 other than the propagating surface zone 112a has a propagating surface zone facing region 152a, which faces the propagating surface zone 112a with a predetermined gap S therebetween, and the electro-acoustic transducing element 114 is formed in the propagating surface zone facing region 152a of the base 152. The dimensions of the electro-acoustic transducing element 114 and the arrangement of the electro-acoustic transducing element 114 with respect to the propagating surface zone 112a are identical to those in the case where the electro-acoustic transducing element 114 is directly formed in the propagating surface zone 112a of the surface acoustic wave device according to each of the sixth embodiment and its first and second modifications.

In the case where the electro-acoustic transducing element 114 is a ladder shaped electrode 122 such as a comb shaped electrode, it is preferable that the predetermined gap S is equal to or smaller than ¼ of an arrangement pitch P (refer to FIG. 17) of a plurality of line elements (terminals) in a pattern of the ladder shaped electrode 122. When the predetermined gap S is greater than ¼ of the arrangement pitch P (refer to FIG. 17), it becomes difficult for the electro-acoustic transducing element 114 to always reliably excite a desired surface acoustic wave along the propagating surface zone 112a along the outer surface of the three-dimensional substrate 112.

The surface acoustic wave device 150 according to the ninth embodiment can be used in the same manner as that in the three-dimensional substrate 112 of each of the sixth embodiment and its first or second modifications. Moreover, in the case where the electro-acoustic transducing element 114 faces the propagating surface zone 112a along the outer surface of the three-dimensional substrate 112 with the predetermined gap S therebetween, an adverse effect, which may be generated by the electro-acoustic transducing element 114 directly formed in the propagating surface zone 112a on the outer surface of the three-dimensional substrate 112 and which may very slightly affect the surface acoustic wave excited along the propagating surface zone 112a and propagating along the propagating surface zone 112a, can be eliminated. Consequently, a change in the surface acoustic wave propagating along the propagating surface zone 112a can be detected more precisely.

Further, also in the surface acoustic wave device 150 according to the ninth embodiment, as in the modification of the seventh embodiment described above with reference to FIG. 23, the propagating surface zone facing region 152a of the base 152 can be faced an intersecting region of a plurality of propagating surface zones 112a along a plurality of outermost circumferential lines 112b that can be specified on the outer surface of the three-dimensional substrate 112. In addition, a common excitation electro-acoustic transducing element 114' can be formed on the propagating surface zone facing region 152a so as to face the above-described intersecting region of the plurality of propagating surface zones 112a along the outer surface of the three-dimensional substrate 112 with a predetermined gap S therebetween. Further, a propagating surface zone facing region of an additional base similar to the base 152 having the propagating surface zone facing region 152a can be faced each of the plurality of propagating surface zones 112a other than the above-described intersecting region. In addition, a receiving electro-acoustic transducing element 114" can be formed on the propagating surface zone facing region of the additional base so that the receiving electro-acoustic transducing element 114" faces each of the plurality of propagating surface zones 112a along the outer surface of the three-dimensional substrate 112 other than the above-described intersecting region with a predetermined gap S therebetween. Also in this case, the surface acoustic device configured as described above can be used as an environmental difference detecting apparatus capable of more precisely detecting an environmental difference, as in the surface acoustic wave device 130 according to the modification of the seventh embodiment described previously with reference to FIG. 23.

Tenth Embodiment

Figure 27:
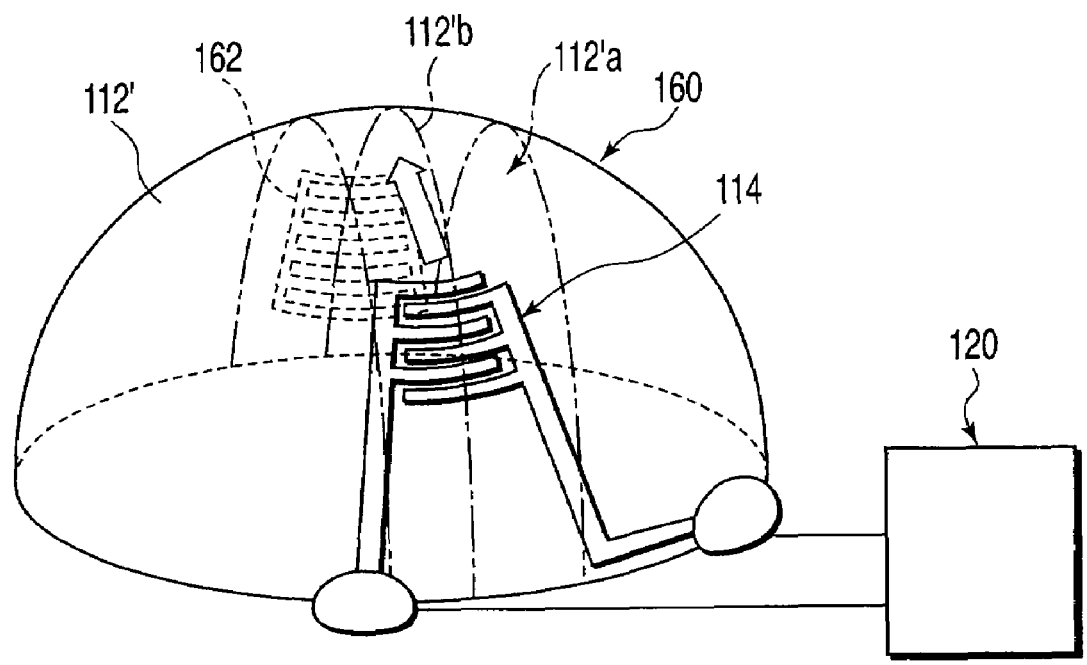
FIG. 27 is a perspective view schematically showing a surface acoustic wave device according to a tenth embodiment of the present invention.

Now, a tenth embodiment of a surface acoustic wave device according to the present invention will be described in detail with reference to FIG. 27.

A surface acoustic wave device 160 according to the tenth embodiment comprises a three-dimensional substrate 112' having a semispherical shape, and an outer surface of the three-dimensional substrate 112' includes a propagating surface zone 112'a made of at least a part of a continuous annular curved surface along which a surface acoustic wave can propagate.

A whole of the semi-spherically shaped three-dimensional substrate 112' is formed of a $LiNbO_3$ crystal, a $LiTaO_3$ crystal, or a quartz crystal, as the three-dimensional substrate 112 according to each of the sixth embodiment and its first and second modification. At least one outermost circumferential line 112'b serving as a reference for extending the propagating surface zone 112'a along a line of intersection between at least one of a plurality of crystal faces, which are specific to a kind of crystal forming the three-dimensional substrate 112' of the surface acoustic wave device 160 according to the tenth embodiment, and the outer surface thereof is specified on the outer surface of the three-dimensional substrate 112', in the same manner as in the case where the outermost circumferential line 112b serving as the reference for extending the propagating surface zone 112a along the line of intersection between at least one of a plurality of crystal faces, which are specific to a kind of crystal forming the three-dimensional substrate 112 of each of the above described sixth embodiment and its first and second modifications, and the outer surface thereof is specified on the outer surface of the three-dimensional substrate 112. And, the outermost circumferential line 112'b is preferably included in the range of the propagating surface zone 112'a.

A method for specifying the outermost circumferential line 112'b serving as the reference for extending the propagating surface zone 112'a along the outer surface of the three-dimensional substrate 112' of this embodiment is identical to that for specifying the outermost circumferential line 112b on the outer surface of the three-dimensional substrate 112 according to each of the above-described sixth embodiment and its first or second modifications.

Further, the electro-acoustic transducing element 114 is directly formed in the propagating surface zone 112'a on the outer surface of the three-dimensional substrate 112' of the present embodiment so as to propagate the surface acoustic wave along the outermost circumferential line 112'b in the range of the propagating surface zone 112'a along the outer surface of the three-dimensional substrate 112' of the present embodiment while keeping its energy of, for example, 80% or more per one circulation, and the above described electro-acoustic transducing element control unit 120 is connected to the electro-acoustic transducing element 114.

In this embodiment, a surface acoustic wave reflector 162 is formed at a position distant from the electro-acoustic transducing element 114 in a propagation direction of a surface acoustic wave which is excited in the range of the propagating surface zone 112'a by the electro-acoustic transducing element 114 and which propagates along the outermost circumferential line 112'b in the range of the propagating surface zone 112'a. The surface acoustic wave reflector 162 reflects the surface acoustic wave propagated from the electro-acoustic transducing element 114 toward the surface acoustic wave reflector 162 along the propagating surface zone 112'a so as to return the electro-acoustic transducing element 114 along the propagating surface zone 112'a in the same passage.

Also, in this embodiment, a portion of the outer surface other than the propagating surface zone 112'a may be formed in an arbitrary shape as long as the propagating surface zone 112'a is specified in accordance with the predetermined method described previously.

Further, in this embodiment, a portion of the three-dimensional substrate 112' other than the propagating surface zone 112'a is supported on a base not shown.

In this embodiment, the acoustic surface wave, which is excited along the propagating surface zone 112'a made of a part of the annular shaped curved surface by the electro-acoustic transducing element 114 and which propagates along the propagating surface zone 112'a without attenuating significantly, changes in response to a variety of changes in a fluid (gas or liquid) including in an outer space that is an environment, with which the propagating surface zone 112'a along the outer surface of the three-dimensional substrate 112' comes into contact. And, the surface acoustic wave device 160 of the present embodiment can detect a change in the environment, i.e., a difference in the environment, by receiving the change in the signal, which is generated from the electro-acoustic transducing element 114, in the electro-acoustic transducing element control unit 120.

Further, in this embodiment, as in the surface acoustic wave device 130 of the seventh embodiment described above with reference to FIG. 22, a plurality of electro-acoustic transducing elements 114, each of which is connected to the electro-acoustic transducing element control unit 120, can be formed along a plurality of propagating surface zones 112'a along a plurality of outermost circumferential lines 112'b aligned with a plurality of lines of intersection between a plurality of crystal faces, which are specific to the crystal forming the three-dimensional substrate 112', and the outer surface thereof, with excluding intersecting portions, at which the plurality of propagating surface zones 112'a intersect with each other.

In this case, the surface acoustic wave reflector 162 is mounted at a position opposed to the surface acoustic transducing element 114 in each of the plurality of propagating surface zones 112'a excluding an intersection portion, with which other propagating surface zone 112'a intersects.

Further, in the present embodiment, as in the surface acoustic wave device 130 of the modification of the seventh embodiment described above with reference to FIG. 23, a common excitation electro-acoustic transducing element 114' can be formed at an intersection region of the plurality of propagating surface zones 112'a along the outer surface of the three-dimensional substrate 112'. At the same time, a receiving electro-acoustic transducing element 114" can be formed along each of the plurality of propagating surface zones 112'a excluding the intersection region, instead of the surface acoustic wave reflector 162.

Furthermore, as in the surface acoustic wave device 140 of the eighth embodiment described above with reference to FIG. 24, this embodiment can be modified such that the propagating surface zone 112a made of at least a part of the annular curved surface and including the outermost circumferential line 112b is specified on, for example, a semi-spherically shaped recessed portion or an inner surface of a semi-spherically shaped cavity formed on or in the three-dimensional substrate 112, and that the electro-acoustic transducing element 114 and the surface acoustic wave reflector 162 are mounted along the propagating surface zone 112a so as to be spaced from each other and opposed to each other along the outermost circumferential line 112a.

Still furthermore, in the present embodiment, as in the surface acoustic wave device 150 of the ninth embodiment described above with reference to FIGS. 25 and 26, the electro-acoustic transducing element 114 can be formed on the above-descried base (not shown) so as to face the propagating surface zone 112'a with the predetermined gap S therebetween, instead of directly forming the electro-acoustic transducing element 114 in the propagating surface zone 112'a of the three-dimensional substrate 112'.

Alternatively, the common excitation electro-acoustic transducing element 114' can be formed on the above-descried base (not shown) so as to face the intersection region of the plurality of propagating surface zones 112'a along the outer surface of the electro-acoustic transducing three-dimensional substrate 112', and, at the same time, the receiving electro-acoustic transducing element 114" can be formed on the above-descried base (not shown) excluding the intersection region so as to face each of the propagating surface zone 112'a with the predetermined gap S therebetween, instead of directly forming the electro-acoustic transducing three-dimensional substrate 112' element 114 in the propagating surface zone 112'a of the three-dimensional substrate 112'.

Yet furthermore, another electro-acoustic transducing element 114 connected to the electro-acoustic transducing element control unit 120 described previously can be used instead of the surface acoustic wave reflector 162.

A surface acoustic wave device is used as a delay line, an oscillator element, a resonator element, a frequency selector element, for example, as a part of an environmental difference detecting apparatus for detecting a variety of environmental differences, the detecting apparatus including a chemical sensor, a biological sensor, and a pressure sensor, or alternatively, as a remote tag, etc.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surface acoustic wave device, comprising:
 a three-dimensional substrate having a surface, which includes at least a part of an annular curved surface formed with a continuous curved surface on which a surface acoustic wave propagates; and
 an electro-acoustic transducing element, which excites the surface acoustic wave along the surface, which propagates the surface acoustic wave along the surface, and which receives the surface acoustic wave propagating along the surface,
 wherein the three-dimensional substrate is made of a $Bi_{12}SiO_{20}$ crystal, and,
 along the surface of the three-dimensional substrate, the electro-acoustic transducing element propagates the excited surface acoustic wave along a line of intersection between a crystal face of the $Bi_{12}SiO_{20}$ crystal and the surface thereof, the line of intersection defined as an outermost circumferential line of the surface.

2. A surface acoustic device according to claim 1, wherein the surface of the three-dimensional substrate has at least a part of a spherical surface.

3. A surface acoustic device according to claim 2, wherein a transmitting and receiving portion of the electro-acoustic transducing element, which excites the surface acoustic wave along the surface of the three-dimensional substrate, which propagates the surface acoustic wave along the surface, and which receives the surface acoustic wave propagating along the surface, is arranged to the surface of the three-dimensional substrate to include a part of the line of intersection.

4. A surface acoustic device according to claim 1, wherein, on the surface, a curved surface on which the surface acoustic wave propagates, is continuous in an annular shape, and the electro-acoustic transducing element excites the surface acoustic wave along the surface and propagates and circulates the surface acoustic wave along the line of intersection.

5. A surface acoustic device according to claim 4, wherein the surface of the three-dimensional substrate is a spherical surface.

6. A surface acoustic device according to claim 5, wherein a transmitting and receiving portion of the electro-acoustic transducing element, which excites the surface acoustic wave along the surface of the three-dimensional substrate, which propagates the surface acoustic wave along the surface, and which receives the surface acoustic wave propagating along the surface, is arranged to the surface of the three-dimensional substrate to include a part of the line of intersection.

7. A surface acoustic device according to claim 1, wherein, in a direction intersecting with an extending direction of the line of intersection along the surface, the electro-acoustic transducing element excites the surface acoustic wave along the surface and propagates the excited surface acoustic wave along the line of intersection while keeping energy of the surface acoustic wave by 80% or more per one circulation, and a dimension of the electro-acoustic transducing element, which receives the surface acoustic wave, is equal to or smaller than $1/1.5$ of a radius of curvature of a curved surface extending in a direction orthogonal to the line of intersection on the surface.

8. A surface acoustic device according to claim 7, wherein in that the electro-acoustic transducing element is arranged along the surface so that an orientation, along which a flow density of energy of a surface acoustic wave emitted from the electro-acoustic transducing element along the line of intersection becomes maximum, is equal to or smaller than 20° with respect to the line of intersection corresponding thereto.

9. A surface acoustic device according to claim 1, wherein the electro-acoustic transducing element is formed along a propagating surface zone of the surface of the three-dimensional substrate, along which the surface acoustic wave propagates.

10. A surface acoustic device according to claim 1, wherein the electro-acoustic transducing element comprises a ladder shaped electrode, and the ladder shaped electrode is configured so that a line, which is along the surface and orthogonal to a transmitting and receiving portion in each of a plurality of terminals of the ladder shaped electrode, the transmitting and receiving portion enabling to excite the surface acoustic wave along the surface and to receive the surface acoustic wave propagating along the surface, is included in a range equal to or smaller than 10° with respect to the line of intersection corresponding thereto.

11. A surface acoustic device according to claim 10, wherein an arrangement pitch of the plurality of terminals of the ladder shaped electrode in a direction along the line of intersection is equal to or smaller than $1/10$ of a radius of curvature of the line of intersection.

12. A surface acoustic device according to claim 1, wherein the surface of the three-dimensional substrate is an outer surface of the three-dimensional substrate.

13. A surface acoustic device according to claim 1, wherein the three-dimensional substrate has a recessed portion or hollow portion, and the surface is the recessed portion or an inner surface of the hollow portion of the three-dimensional substrate.

14. An environmental difference detecting apparatus, wherein, along the surface of the surface acoustic wave device according to any one of the claims 1 to 6, a plurality of electro-acoustic transducing elements excite surface acoustic waves, propagate the surface acoustic waves along a plurality of lines of intersection of the surface of the surface acoustic wave device, and receive the propagated surface acoustic waves to output reception signals;

the reception signals outputted from the plurality of electro-acoustic transducing elements are compared with each other; and an environmental difference in a plurality of portions of a space, with which the plurality of portions along the surface propagating the plurality of surface acoustic waves come into contact, is detected.

* * * * *